US007445785B2

(12) United States Patent
Cavanagh et al.

(10) Patent No.: US 7,445,785 B2
(45) Date of Patent: Nov. 4, 2008

(54) INFECTIOUS BRONCHITIS VIRUS WITH AN ALTERED SPIKE GENE

(75) Inventors: David Cavanagh, Newbury (GB); Paul Britton, Newbury (GB); Ian Tarpey, St. Ives (GB)

(73) Assignees: Intervet International B.V., Boxmeer (NL); Institute for Animal Health, Berkshire (GB)

( * ) Notice: Subject to any disclaimer, the term of this patent is extended or adjusted under 35 U.S.C. 154(b) by 0 days.

(21) Appl. No.: 10/547,219

(22) PCT Filed: Mar. 3, 2004

(86) PCT No.: PCT/EP2004/050247

§ 371 (c)(1),
(2), (4) Date: Jan. 11, 2007

(87) PCT Pub. No.: WO2004/078203

PCT Pub. Date: Sep. 16, 2004

(65) Prior Publication Data

US 2007/0154489 A1   Jul. 5, 2007

(30) Foreign Application Priority Data

Mar. 3, 2003   (EP)   .................. 03075623

(51) Int. Cl.
*A61K 39/215*   (2006.01)
*C07K 14/165*   (2006.01)

(52) U.S. Cl. .............. 424/199.1; 424/221.1; 424/222.1; 424/184.1

(58) Field of Classification Search ........... None
See application file for complete search history.

(56) References Cited

FOREIGN PATENT DOCUMENTS

| WO | WO 98/49195 | 11/1998 |
| WO | WO 01/64244 A2 | 9/2001 |
| WO | WO 02/092827 A2 | 11/2002 |

OTHER PUBLICATIONS

Evans, et al. Utilising a defective IBV RNA for heterologous gene expression with potential phrophylactic application. Adv Exp. Med Biol. 1998; 440:687-92.*
Niesters, et al. The peplomer protein sequence of the M41 strain of coronavirus IBV and its comparison with Beaudette strains. Vir. Res. 1986; 5(2-3): 253-63.*
Cook, et al. A survey of the presence of a new infectious bronchitits virus designated 4/91 (793B). Veterin. Rec. 1996; 138(8):178-80.*
Wang, Xiuqing et al. "Construction and Immunogenicity Studies of Recombinant Fowl Poxvirus . . ." Avian Diseases (2002) 46:831-838.
Song, Chang-Seon, et al. "Induction of protective immunity in chickens vaccinated with infectious bronchitis virus S1 glycoprotein . . ." J. of General Virology (1998) 79:719-723.
Wang, Li, et al. "Experimental confirmation of recombination upstream of the S1 hypervariable region of infectious bronchitis . . ." Virus Research (1997) 49:139-145.
Casais, Rosa et al. "Recombinant Avian Infectious Bronchitis Virus Expressing a Heterologous Spike Gene Demonstrates . . ." J. of Virology (Aug. 2003) V77, N16, p. 9084-9089.

* cited by examiner

*Primary Examiner*—Mary E. Mosher
*Assistant Examiner*—Stuart W Snyder
(74) *Attorney, Agent, or Firm*—William M. Blackstone

(57) ABSTRACT

The present invention provides a vaccine for use in the protection of poultry against infectious bronchitis comprising an attenuated infectious bronchitis virus (IBV) and a pharmaceutical acceptable carrier or diluent, characterized in that the attenuated IBV comprises a heterologous spike gene. Such a vaccine is based on IBV strain Beaudette that is able to express a spike gone derived from a different IBV strain. The vaccines provided by the present invention also allow the administration via the in ovo route.

10 Claims, 12 Drawing Sheets

Figure 8

INFECTIOUS BRONCHITIS VIRUS WITH AN ALTERED SPIKE GENE

RELATED APPLICATIONS

This application is a national stage of PCT/EP2004/050247 filed Mar. 3, 2004, which claims priority to EP Application 03075623.3 filed Mar. 3, 2003, both of which are included herein by reference in their entirety.

The present invention is concerned with a vaccine for use in the protection of poultry against infectious bronchitis (IB) comprising an attenuated infectious bronchitis virus (IBV) and a pharmaceutical acceptable carrier or diluent, a method for the preparation of such a vaccine and the use of an attenuated IBV for the manufacture of a vaccine for the protection of poultry against IB for in ovo administration.

IBV is a member of the genus *coronavirus*, family Coronaviridae. It has a positive sense, single-stranded RNA genome of approximately 28 000 nucleotides associated with a nucleocapsid protein, N, surrounded by a lipid membrane/envelope. Three other viral proteins are associated with the envelope: the large spike glycoprotein, S; a smaller integral membrane protein, M; and the E protein, the smallest of the envelope associated proteins.

The *coronavirus* S protein is a type I glycoprotein which oligomerises in the endoplasmic reticulum to form trimers which constitute the *coronavirus* virion spikes observable by electron microscopy. The S protein is assembled into virion membranes, possibly through noncovalent interactions with the M protein, but is not required for formation of *coronavirus* virus-like particles. Following incorporation into *coronavirus* particles, determined by the carboxy-terminal domain, the S glycoprotein is responsible for binding to the target cell receptor and fusion of the viral and cellular membranes, fulfilling a major role in the infection of susceptible cells. Furthermore, the IBV spike protein is involved in the induction of a protective immune response when inoculated into chickens (for a review see Cavanagh, in: The Coronaviridae; ed: S. G. Siddell, Plenum Press, 73-113, 1995).

All *coronavirus* S glycoproteins, consist of four domains; a signal sequence, that is cleaved during synthesis, the ectodomain which is present on the outside of the virion particle, the transmembrane region responsible for anchoring the S protein into the lipid bilayer of the virion particle, and the cytoplasmic tail that might interact with other IBV proteins, such as the membrane protein (E) and integral membrane protein (M). The IBV S glycoprotein (1162 amino acids) is cleaved into two subunits, S1 (535 amino acids 90-kDa) and S2 (627 amino acids 84-kDa). The C-terminal S2 subunit associates noncovalently with the N-terminal S1 subunit and contains the transmembrane and C-terminal cytoplasmic tag domains. The S1 subunit contains the receptor-binding activity of the S protein.

In previous studies with other *coronaviruses*, murine hepatitis virus (MHV) and transmissible gastroenteritis virus (TGEV), a spike gene of a (virulent) donor virus strain was used to replace the spike gene of a receiver virus strain to investigate the determinants of pathogenesis and cell tropism. These studies showed that both the in vitro properties (cell tropism) and in vivo properties (virulence) of the donor virus strain were acquired by the receiver virus strain. It was concluded that the spike gene is a determinant of cell tropism and virulence (Phillips et al., J. Virol. 73, 7752-7760, 1999; Sanchez et al., J. Virol. 73, 7607-7618, 1999; Des Sarma et al., J. Virol. 74, 9206-9213, 2000; Navas et al., J. Virol. 75, 2452-2457, 2001 and Kuo et al., J. Virol. 74, 1393-1406, 2000; international patent application WO 01/39797). International patent application WO 98/49195 discloses a *coronavirus* (e.g. MHV) in which a part of the spike protein gene has been replaced by the corresponding part of the spike protein gene of an unrelated *coronavirus* (e.g. FIPV), thereby acquiring another cell substrate specificity allowing the recombinant virus to target other cell types.

Infectious bronchitis is an acute, highly contagious respiratory disease of the domestic fowl (chicken), caused by IB virus. Clinical signs of IB include sneezing/snicking, tracheal rates, nasal discharge and wheezing. Clinical signs are more obvious in chicks than in adult birds. The birds may appear depressed and consume less food. Meat-type birds have reduced weight-gain, whilst egg-laying birds lay fewer eggs. The respiratory infection predisposes chickens to secondary bacterial infections, which can be fatal in chicks. The virus can also cause permanent damage to the oviduct, especially in chicks, leading to reduced egg production and quality, and kidney, sometimes leading to kidney disease, which can be fatal.

Both live and inactivated virus vaccines are used in IB vaccination. To date, the most efficacious vaccines are live attenuated viruses empirically produced following blind repeated passages through embryonated eggs until a desired balanced degree of attenuation and immunogenicity has been achieved. Such vaccines are ill-defined genetically and the molecular basis of the attenuation is unknown. Disadvantageously, upon serial passaging the immunogenicity of the virus decreases which often results in safe but less efficacious vaccine viruses. Achieving a 'balanced' degree of attenuation—sufficient so as not to be pathogenic but not excessive to the point that it would fail to induce strong immune responses—is a trial and error approach that renders the outcome of this conventional attenuation approach uncertain.

As indicated above, one of the biologic properties of IBV is that it becomes avirulent and less immunogenic with successive passages of the virus in embryos. The Beaudette strain of IBV is one such high embryo passage, (over-)attenuated, virus that is not considered to be immunogenic (Geilhausen et al., Arch Gesamte Virusforsch 40, 285-290, 1973).

In a recently published patent application (WO 02/092827) the development of live, attenuated *coronaviruses* by means of recombinant DNA techniques is disclosed. It is suggested therein that the introduction of deletions in non-essential genes on *coronavirus* genomes results in the attenuation of these viruses.

IBV exhibits great antigenic variation, initially recognized as different serotypes. Serotypic strain classification of IBV strains is based on the ability of one strain to induce virus neutralizing antibodies effective against another strain (Cook et al. Avian Pathol. 13, 733-741, 1984). The most variable protein of IBV is the spike protein. It defines the serotype and is the major inducer of protective immune responses. An IBV vaccine virus of one serotype induces immune responses that often protect poorly against IBV of other serotypes, because of the differences in the S proteins. Consequently IB vaccines have been developed against many serotypes. However, previously unknown serotypes are continually emerging, creating a requirement for new, homologous vaccine viruses.

Live IBV vaccines are usually administered to hatched chickens. Administration can be individually by eye drop or intranasally, but these routes are expensive because of the labour needed for their administration, in particular in large broiler flocks. Mass application methods, including spray and drinking water, are also frequently used, but problems in attaining a uniform vaccine application and inactivation of the vaccine virus have been observed.

The use of vaccines as embryo vaccines (so-called in ovo vaccines) has been suggested previously (Sharma et al; Avian diseases 29, 1155-1169, 1985).

In ovo vaccination, in principle, could be advantageous due to the early age of resistance to the specific disease and the administration of a uniform dose of vaccine into each egg using semiautomatic machines with multiple injection heads.

Usually conventional vaccines for post-hatch vaccination of birds cannot be used for in ovo vaccination, because late stage embryos are highly susceptible to infection with most vaccine viruses examined. For instance, vaccine strains of IBV and Newcastle disease virus (NDV) that are used routinely as vaccines in newly hatched chicks are lethal for embryos following in ovo inoculation. Examples of commercially available post-hatch vaccines that cannot be used for in ovo vaccination due to their adverse effect on hatchability of the embryonated eggs are Poulvac© IB, Nobilis IB Ma5© and Nobilis IB 4/91©.

International patent application WO 01/64244 discloses that the Poulvac© IB vaccine can be used for in ovo administration provided it is applied at a very low dose ($10^{-1.0}$-$10^{2.0}$ $EID_{50}$/egg). Wakenell et al., (J. Vet. Res., 47, 933-938, 1986) discloses that passaging an IB vaccine virus in tissue culture rendered the virus apathogenic for embryos. However, challenge virus could still be isolated from vaccinated commercial chicks.

In view of the above it is clear that there exists a need for IBV vaccines that are both safe and afford adequate protection against virulent field strains, in particular of emerging serotypes, and that can be made without using the conventional empirical approach for IBV vaccine preparation.

Furthermore, there is a need for a safe and efficacious IBV vaccine that can be administered via the in ovo route without having a negative impact on the hatchability of the vaccinated embryonated egg.

BRIEF SUMMARY OF THE INVENTION

The present invention provides an IBV vaccine that is based on an attenuated IBV strain Beaudette that is able to express a spike protein derived from an IBV strain, for example a field strain, that is different from the spike protein of the Beaudette strain. This new attenuated IBV vaccine strain is better equipped for combating IBV infections that an attenuated IBV strain obtained by conventional methods, because in can express a spike protein that is homologous to that of a (virulent) field virus while remaining avirulent.

BRIEF DESCRIPTION OF THE DRAWINGS

Legends to the Figures

DESCRIPTION OF THE PREFERRED EMBODIMENTS

Figure 1:
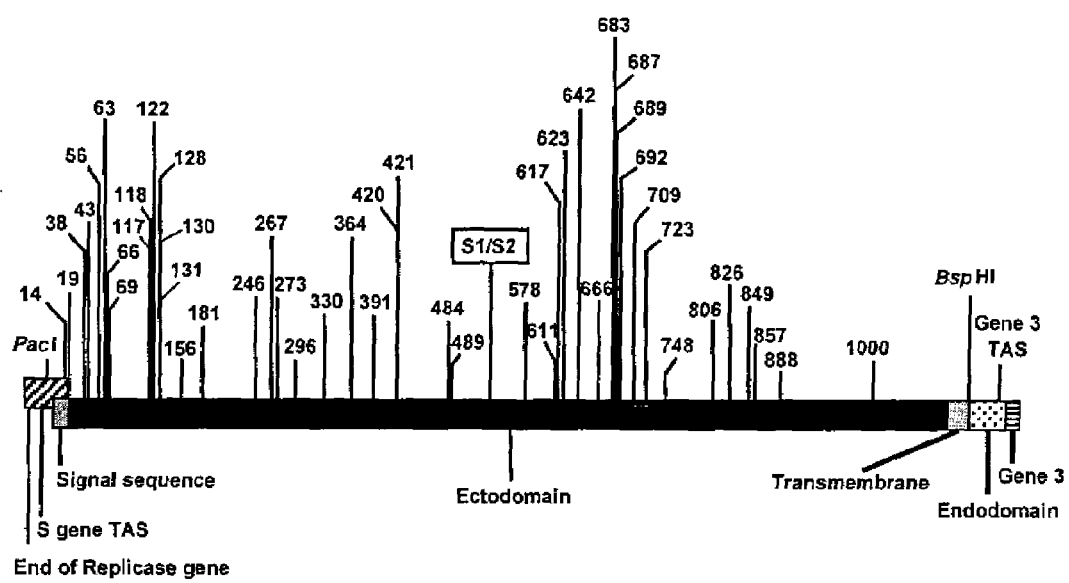
FIG. 1. Schematic diagram of the IBV S gene. The 5' end of the S gene overlaps the 3' end of the replicase gene. The four domains of the S protein, the position of the S1/S2 cleavage point and the positions of the PacI and BspHI restriction sites, the S gene TAS, the gene 3 TAS and the start of gene 3 are shown. The numbers refer to the positions of the amino acid differences between IBV Beaudette-CK and M41-CK-S protein sequences within the chimaeric S gene sequences, resulting from non-synonymous substitutions following exchange of the two S gene sequences.

The present invention provides a vaccine for use in the protection of poultry against infectious bronchitis comprising an attenuated infectious bronchitis virus (IBV) and a pharmaceutical acceptable carrier or diluent, characterized in that the attenuated IBV is IBV strain Beaudette that comprises a heterologous IBV spike gene that is protective against IBV infection and may be safe for in-ovo administration.

It is demonstrated in the Examples that IBV strain Beaudette that is known to be attenuated, but poorly protective, is rendered highly protective by the insertion of a spike gene of a virulent virus (IBV M41), whereas the level of attenuation of the attenuated IBV strain was not affected (Examples 3 and 4). In particular, the latter property of the recombinant IBV was unexpected as it has been demonstrated for other *coronaviruses* that the S gene is a determinant of virulence and that replacing the S gene in mild *coronaviruses* by a S gene of a virulent *coronavirus* rendered the recombinant *coronaviruses* virulent the absence of an increase of virulence of the recombinant IBV after replacement of the S genes is the more surprising if it is taken into account that the recombinant attenuated IBV does acquire the cell tropism of the virulent IBV in vitro (Example 2).

IBV strain Beaudette was originally isolated by Beaudette and Hudson (J. Am. Vet. Med. A. 90, 51-60, 1937) and passaged several hundred times in chicken embryos, it is commonly refereed to as a "chicken embryo adapted" or "egg adapted" strain. The highly egg-adapted Beaudette strain is a-pathogenic for post-hatch administration, causes little detectable damage to ciliated epithelium of trachea and replicates predominantly in the subepithellal cells, but is known to be extremely pathogenic for 9-12-day-old embryos. Furthermore, IBV Beaudette is known to be a strain with a poor immunogenicity (Arch Gesamte Virusforsch 40, 285-290, 1973). IBV strain Beaudette is obtainable from the ATCC (accession no. VR-22), and is commonly used in laboratories throughout the world although these viruses may have slight sequence differences due to their individual passage histories. For example, the nucleotide sequences of the spike genes of different IBV Beaudette isolates display an identity of 99% or more. A region on the genome of IBV strain Beaudette that distinguishes this IBV strain from other IBV strains is a region (nucleotides 26500-27499; numbering according to Casais et al., 2001, supra, accession No. AJ311317) located at the 3'-terminal end of the genome that starts within the nucleoprotein gene and ends within the 3' untranslated region (UTR). An IBV strain Beaudette to be used in the present invention is an IBV that display a nucleotide sequence identity of 99% or more in this region with the corresponding region in the IBV strain Beaudette specifically used herein (BeauR, accession No. AJ311317). The nucleotide sequences of the corresponding region in other IBV strains differ significantly (63-95%) from those in IBV strain Beaudette. The nucleotide sequence identities referred to herein are determined by the alignment program ClustalX using the multiple alignment mode, Thomson et al., NAR 24, 4876-4882, 1997, and analysed by Genedoc, version 2.6.002, accessible from www.psc.edu/biomed/genedoc.

In a particularly preferred embodiment of the present invention a vaccine is provided that is further characterized in that the attenuated IBV is the Beaudette strain Beau-CK or BeauR (deposited at the CNCM of the Institute Pasteur, Paris, France on 27 Feb., 2004 under accession no. I-3167). BeauR is a recombinant IBV produced from an infectious RNA transcribed from a full length cDNA of Beau-CK. The complete genomic sequence analyses for Beau-CK (Boursnell at al., J. Gen. Virol. 68, 57-77, 1987, accession No. M95169) and BeauR have been determined (Casais et al., 2001, supra; accession No. AJ311317).

A recombinant attenuated IBV comprising a heterologous spike gene to be used in a vaccine according to the invention can be prepared by means of the reverse genetics system described in Casais et al., (2001, supra). This system allows the preparation of recombinant IBV (rIBV) by assembling (mutated) IBV full-length cDNA in vitro, followed by direct cloning into a vaccinia virus genome, and recovering rIBV after in situ synthesis of infectious IBV RNA by using bacteriophage T7 RNA polymerase expressed from a recombinant fowlpox virus.

By "an heterologous spike (S) gene" is meant a S gene derived from an IBV strain (the donor strain) that is different from the specific attenuated IBV strain Beaudette that receives that S gene (the receiver strain) and that encodes a S protein having an amino acid sequence that is different compared to the S protein encoded by the S gene of the IBV strain Beaudette. The donor—and receiver strain may be of the same or different IBV serotypes). Such a recombinant IBV is based on the genome of a single IBV (receiver) strain, the only difference, in essence, being the S gene that is derived from a different IBV (donor) stain.

Furthermore, in the context of the present invention it is not required that the complete spike gene has to be transferred from the donor-to the receiver IBV strain. A spike gene is considered to be heterologous in case the fragment of the spike gene that encodes the ectodomain of the spike protein, or a functional part thereof that is able to induce a protective immune response, is derived from the donor IBV strain.

In a preferred embodiment of the present invention the vaccine is based on an IBV strain Beaudette that comprises a spike gene of which the fragment encoding the ectodomain or a functional part thereof, in particular the S1 polypeptide, is derived from a different donor IBV, whereas the fragment encoding the cytoplasmic tail is derived from the receiver IBV strain Beaudette. The advantage of such a "chimaeric" spike gene is that any potential problems between the interaction of the cytoplasmic tail domain of the spike protein with the other IBV proteins are avoided as both are native to the receiver IBV.

In general, the signal sequence, the ectodomain, the transmembrane region and the cytoplasmic tail domain of IBV spike proteins cover the amino acid fragments 1-18, 19-1091, 1092-1119 and 1120-1162, respectively (numbers refer to Beaudette-CK, Casais et al., J. Virol. 75, 12359-12369, 2001; S proteins from other strains of IBV can differ in the number of amino acids due to small deletions and insertions). In addition, also the amino acid sequence at the S1/S2 cleavage site of IBV is well known. For Beaudette the S1 and S2 polypeptides span amino acid 1 (19)-535 and 536-1162, respectively.

Preferably, a spike gene to be used in the present invention is derived from a (virulent) IBV from the field.

Spike genes can be isolated from any available IBV strain irrespective of its serotype by standard techniques commonly used in the art for this purpose. The nucleotide sequences of the spike genes derived from IBV strains of the same serotype are relatively conserved. The maximum nucleotide sequence difference between the spike genes within the same serotype is 10% in the S1 part.

Therefore, with a spike gene of an IBV of a certain serotype is meant a spike gene derived from a strain having the immunological characteristics of that serotype and having a nucleotide sequence that exhibits a maximum of 10% nucleotide sequence difference (in the S1 part) with that of a reference strain of the serotype. Examples of typical reference strains and the nucleotide sequence database accession numbers of their spike gene sequences are M41 (Massachusetts serotype; X04722), NL/D274/78 (D274 serotype; X15832), USA/Arkansas 99 (Ark 99 serotype; L10384), Belgium/B1648 (B1648 serotype; X87238), USA(DE)/072/92 (DE072 serotype; U77298), US(GA)/0470/98 (Georgia 98 serotype; AF274437), UK/4/91 (793B1 serotype; AF093794), USA/Connecticut (Connecticut serotype; L18990) and NL/D1466 (D1466 serotype; M21971).

The cloning of various IBV spike genes is described in Adzhar et al., Avian Path. 26, 625-640, 1997; Shaw et al., Avian Pathol. 25, 607-611, 1996; Binns et al., J. Gen. Viol. 67, 2825-2831, 1986 and Binns et al., J. Gen Virol. 66, 719-726, 1985).

A preferred embodiment of the present invention concerns a vaccine as described above that is based on an attenuated IBV that comprises a spike gene that encodes a spike protein of an IBV Massachusetts serotype, in particular of IBV strain M41.

In a further preferred embodiment the vaccine is based on an attenuated IBV that comprises a spike gene that encodes a spike protein of an IBV 793B serotype, in particular of IBV strain 4/91.

Figure 5:
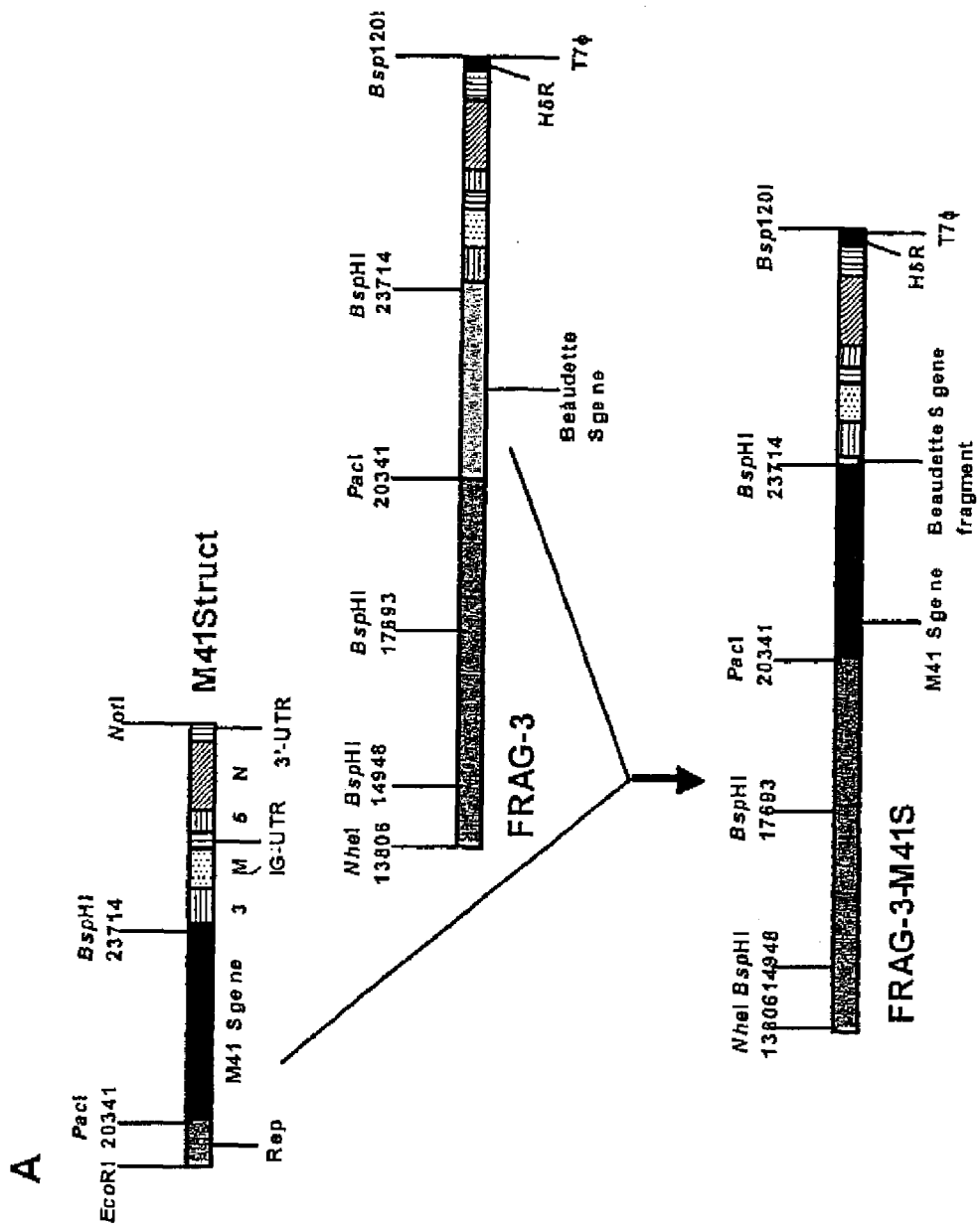
FIG. 5. Schematic diagram for the construction of the chimaeric S gene and production of a full-length IBV cDNA. (A) Replacement of the signal sequences, ectodomain and transmembrane regions of the Beaudette-CK S gene with the corresponding sequence from IBV M41-CK for construction of FRAG-3-M41S. (B) Schematic diagram of the BeauR-M41(S) full-length cDNA composed of FRAG-1, FRAG-2 and FRAG-3-M41S.
Figure 5:
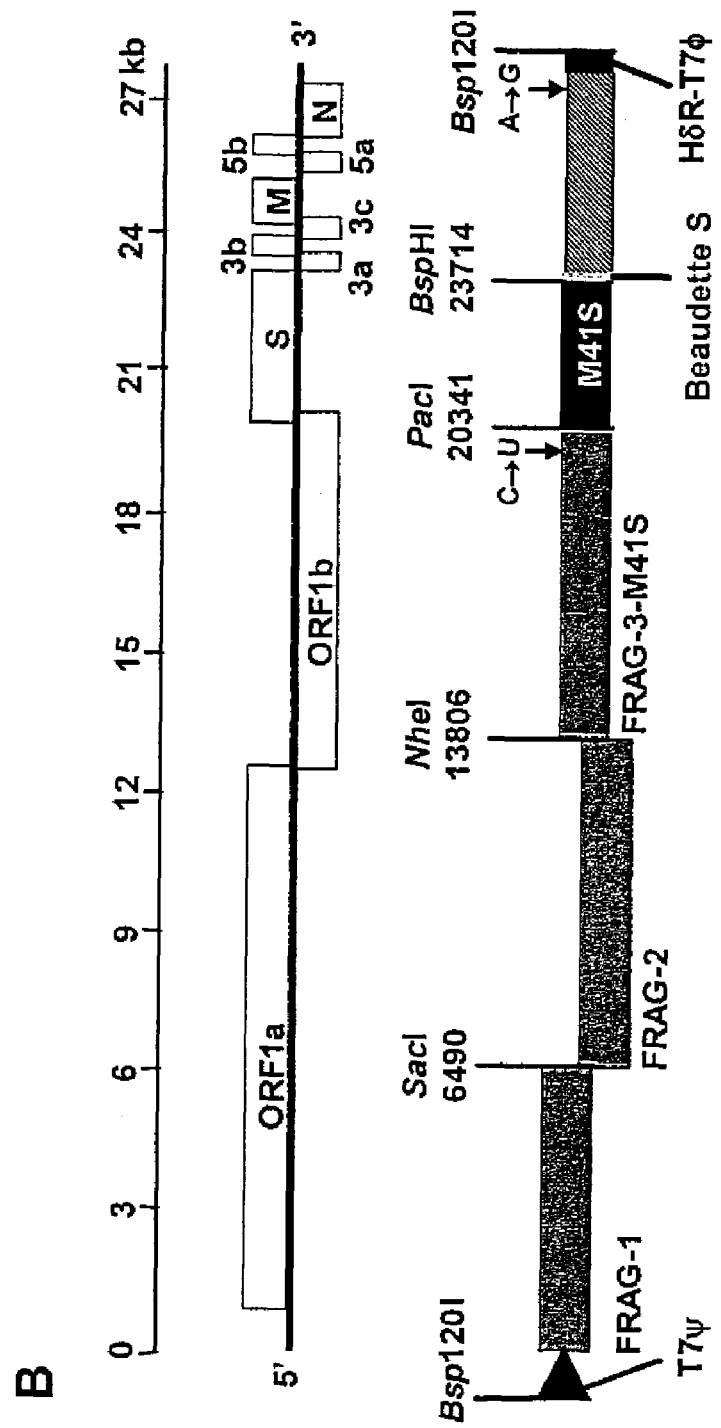

In principle, the IBV strain Beaudette comprising the heterologous spike gene may have this gene inserted in its genome in addition to the spike gene naturally present in the genome. However, in a preferred embodiment of the present invention the vaccine comprises an IBV strain Beaudette in which the heterologous spike gene replaces the original spike gene at its natural position between the replicase gene and gene 3 (FIG. 5).

Until today no IBV vaccine that is both safe and efficacious for in ovo administration is commercially available. The present invention, in particular, demonstrates that a vaccine according to the present invention based on IBV strain BeaudetteR (BeauR) can safely be administered via the in ovo route as well as to hatched chicks and that it at the same time induces a protective immune response. In Example 4 it is shown that this IBV strain BeauR is not lethal for 18 day-old (SPF) embryos and that the hatchability of the inoculated eggs is very high. This property makes IBV strain BeauR suited for receiving a heterologous spike gene and for administering a vaccine according to the invention based on this recombinant IBV strain to a chicken via the in ovo route.

A vaccine according to the present invention can comprise the attenuated IBV in a live or inactivated form, the live form being preferred, i.e. because it does not require adjuvant.

The present invention also provides a solution for the problem of interference that frequently occurs when administering combinations of different live vaccine viruses. The combined administration of two or more vaccine viruses that are the same in essence, but express spike proteins from different (sero)types of IBV, is possible now without the interference of replication of one vaccine virus by the other vaccine virus.

Therefore, the present invention also provides a vaccine as defined above that comprises two or more IBV Beaudette strains that comprise heterologous spike genes of different IBV strains, preferably of IBV strains of different serotypes.

A vaccine according to the invention can be prepared by conventional methods such as those commonly used for the commercially available live- and inactivated IBV vaccines.

Briefly, a susceptible substrate is inoculated with the attenuated IBV and propagated until the virus replicated to a desired titre after which IBV containing material is harvested. Subsequently, the harvested material is formulated into a pharmaceutical preparation with immunising properties.

Every substrate which is able to support the replication of IBV can be used in the present invention, including primary (avian) cell cultures, such as chicken embryo fibroblast cells (CEF), chicken kidney cells (CK), tracheal organ cultures, or mammalian cell lines such as the VERO cell line.

Particularly suitable substrates on which the attenuated IBV can be propagated are SPF embryonated eggs. 9-12 day-old embryonated eggs can be inoculated with, for example 0.1 ml IBV containing allantoic fluid comprising at least $10^{2.0}$ $EID_{50}$ per egg. Preferably, 9- to 12-day-old embryonated eggs are inoculated with about $10^{5.0}$ $EID_{50}$ and subsequently incubated at 37° C. for 12-72 hours. The IBV can be harvested preferably by collecting the allantoic fluid.

The vaccine according to the invention comprises the attenuated IBV together with a pharmaceutically acceptable carrier or diluent custom used for such compositions.

The vaccine containing the live virus can be prepared and marketed in the form of a suspension or in a lyophilised form. Carriers include stabilisers, preservatives and buffers. Diluents include water, aqueous buffer and polyols.

If desired, the live vaccine according to the invention may contain an adjuvant Examples of suitable compounds and compositions with adjuvant activity are the same as those mentioned below for the inactivated IBV vaccine.

Although administration by injection, e.g. intramuscular, subcutaneous of the live vaccine according to the present invention is possible, the vaccine is preferably administered by the inexpensive mass application techniques commonly used for IBV vaccination. For IBV vaccination these techniques include drinking water, aerosol and spray vaccination. Alternatively, administration of the live vaccine can also be individually by eye drop, intratracheal or intranasal.

As outlined above, the present invention also provides an IBV vaccine that can be safely administered via the in ovo route and at the same time is able to induce a protective immune response. The in ovo administration of the vaccine involves the administration of the vaccine to an avian embryo while contained in the egg (for a review on in ovo vaccination see: Ricks et al., Advances in Vet. Med. 41, 495-515, 1999). The vaccine may be administered to any suitable compartment of the egg (e.g. allantois fluid, yolk sac, amnion, air cell or into the embryo) as described in the art (Sharma; Am. J. Vet. Res. 45, 1619-1623, 1984). Preferably the vaccine is administered below the shell (aircell) membrane and chorioallantoic membrane. Usually the vaccine is injected into embryonated eggs during late stages of the embryonation, generally during the final quarter of the incubation period, preferably 3-4 days prior to hatch. In chickens the vaccine is preferably administered between day 15-19 of the 21 day incubation period, in particular at day 17 or 18, most preferably at day 18 of the incubation period.

Subsequently, the vaccinated embryonated eggs are transferred to an incubator to hatch (U.S. Pat. No. 4,458,630, WO 98/56413 and WO 95/35121). Preferably, the whole embryo vaccination process is carried out using high-speed automated vaccination systems, such as the commercially available INOVOJECT®. Such devices are also disclosed in U.S. Pat. Nos. 4,681,063 and 4,903,635, 4,040,388, 4,469,047 and 4,593,646.

In another aspect of the present invention a vaccine is provided comprising the attenuated IBV in an inactivated form. The advantages of an inactivated vaccine are its safety and the high levels of protective antibodies of long duration that can be induced.

The aim of inactivation of the viruses harvested after the propagation step is to eliminate reproduction of the viruses. In general, this can be achieved by well-known chemical or physical means.

An inactivated vaccine according to the invention can, for example, comprise one or more of the above-mentioned pharmaceutically acceptable carriers or diluents suited for this purpose.

Preferably, an inactivated vaccine according to the invention comprises one or more compounds with adjuvant activity. Suitable compounds or compositions for this purpose include aluminium hydroxide, -phosphate or -oxide, oil-in-water or water-in-oil emulsion based on, for example a mineral oil, such as Bayol F® or Marcol 52® or a vegetable oil such as vitamin E acetate, and saponins.

Inactivated vaccines are usually administered by injection, e.g. intramuscularly or subcutaneously.

The vaccine according to the invention comprises an effective dosage of the attenuated IBV as the active component, i.e. an amount of immunising IBV that will induce immunity in the vaccinated birds against challenge by a virulent virus. Immunity is defined herein as the induction of a significantly higher level of protection in a population of birds against mortality and clinical symptoms after vaccination compared to an unvaccinated group.

Typically, the live vaccine for post-hatch administration comprises the attenuated IBV in a concentration of $10^{2.0}$-$10^{8.0}$ embryo infectious dose ($EID_{50}$) per unit dose, preferably in a concentration of $10^{3.0}$-$10^{7.0}$ $EID_{60}$ per unit dose. The dose volume per bird depends on the route of vaccination and the age of the bird. Typically, eye drop vaccines are administered in a volume of 20-100 µl per dose at any age. Spray vaccines may contain the dose in a volume of 100-1000 µl for day-old birds and one dose of a drinking water vaccine usually is diluted in a volume of about 1 ml for each day of age. Inactivated vaccines may contain the antigenic equivalent of $10^{4.0}$-$10^{9.0}$ $EID_{50}$ per unit dose.

The live vaccine for in ovo administration typically comprises an amount of the attenuated IBV of $10^{2.0}$-$10^{8.0}$ $EID_{50}$, preferably $10^{3.0}$-$10^{7.0}$ $EID_{50}$ in a volume of 50-100 µl, preferably 50 µl.

Although, the IBV vaccine according to the present invention may be used effectively in chickens, also other poultry such as turkeys, pigeons, quail, pheasants, guinea fowl and partridges may be successfully vaccinated with the vaccine. Chickens include broilers, reproduction stock and laying stock.

The age of the birds receiving a live or inactivated vaccine according to the invention post-hatch is the same as that of the birds receiving the conventional commercially available live- or inactivated IBV vaccines. For example, broilers may be vaccinated at one-day old or at 1-3 weeks of age, particularly for broilers with high levels of MDA. Laying stock or reproduction stock may be vaccinated initially at 1-10 days of age and boosted with a live or inactivated vaccine at 7-12 or 16-18 weeks of age.

The invention also includes combination vaccines comprising, in addition to the attenuated IBV, a vaccine strain capable of inducing protection against another IBV serotype strain or against another avian pathogen.

Preferably, the combination vaccine additionally comprises one or more vaccine strains of Marek's Disease virus (MDV), Newcastle disease virus (NDV), infectious bursal disease virus (IBDV), egg drop syndrome (EDS) virus, turkey rhinotracheitis virus (TRTV) or reovirus.

EXAMPLES

Example 1

Preparation of Recombinant IBV Beaudette with Heterologous Spike Genes

Recombinant DNA Techniques.

Recombinant DNA techniques used herein were according to standard procedures (Ausubel et al., in: Current Protocols in Molecular Biology, Wiley and Sons Inc, NY, 1987; Sambrook et al., in: Molecular Cloning: A laboratory Manual $2^{nd}$ edition, Cold Spring Harbor Laboratory, NY, 1989) or were used according to the manufacturers' Instructions. All nucleotide and amino acid residue numbers refer to the positions in IBV Beau-R (Casais, 2001, supra, accession No. AJ311317). Cells, viruses, plasmids and bacterial strains used for the preparation of the chimaeric S gene, assembly of full-length IBV cDNA in vaccinia virus, generation of recombinant vaccinia virus and generation of infectious recombinant IBV were as described in Casais et al. (2001, supra).

Construction of chimaeric S gene, assembly/modification of a full-length IBV cDNA in vaccinia virus and generation of recombinant vaccinia virus.

Recombinant IBV Beaudette-M41 Spike Gene

Sequence analysis of the M41-CK S gene identified 72 nt differences when compared to the BeauR S gene sequence of which 50 represented non-synonymous and 22 synonymous substitutions resulting in a total of 47 amino acid differences between the two S glycoproteins. The last non-synonymous substitution results in a premature stop codon within the M41 S gene, so that the M41-CK S glycoprotein is nine amino acids shorter than the Beaudette protein. Apart from the loss of the nine amino acids there were no other amino acid differences between the cytoplasmic domains of the two viruses. Overall, the primary translation products of the two S genes are 1153 and 1162 amino acids for M41-CK and BeauR, respectively, representing an identity of 95.2% between the two S proteins. Comparison of the replicase sequence that overlaps the S gene sequence showed there is only one synonymous mutation with no mutations between the S gene transcription associated sequence (TAS) and the initiation codon of the S gene (FIG. 1). Therefore, the region of the S gene containing the overlapping region of the replicase gene was acquired from M41-CK for generation of the rIBV S gene sequence. However, because the C-terminal ends of the Beaudette and M41 S genes varied, and are potentially involved in interacting with other virion proteins, we retained the last 137 nt of the Beaudette S gene sequence for the rIBV. This would maintain any interaction of the S protein C-terminal domain with the other Beaudette-derived proteins.

Figure 3:
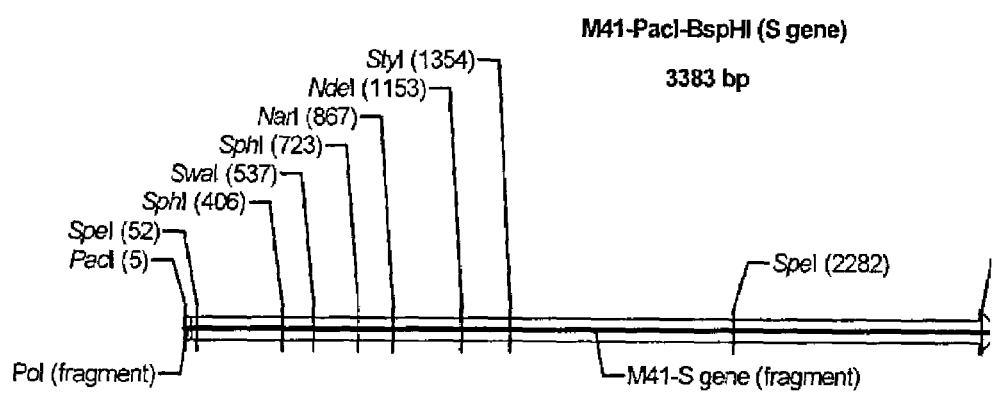
FIG. 3. Schematic structure of the 3383 bp PacI-BspHI cDNA fragment comprising the signal sequence, ectodomain and transmembrane domain of the M41 spike gene. Restriction sites are indicated.
Figure 4:
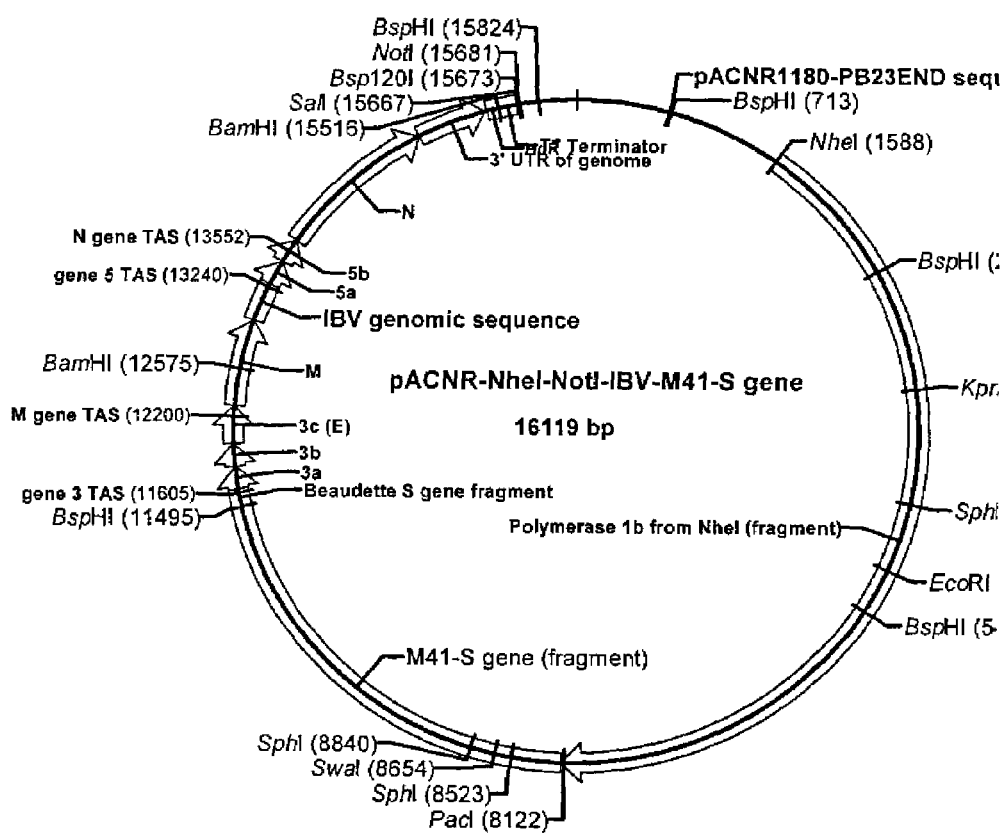
FIG. 4. Schematic structure of plasmid pACNR-NheI-NotI-IBV-M41-S comprising the chimaeric S gene and used as the source of FRAG-3-M41S for generation of an IBV full-length cDNA containing the chimaeric S gene sequences. Restriction sites are indicated.

Plasmid pACNR-NheI-NotI-IBV (FIG. 2) was digested with PacI and SalI and the vector-containing fragment purified and retained. Plasmid pACNR-NheI-NotI-IBV was also digested with BspHI and SalI and the BspHI-SalI fragment purified and retained. Plasmid pM41Struct contained an IBV-derived cDNA sequence, corresponding from within the replicase gene to the poly (A) tail, derived from M41-CK gRNA, in pBluescript SK(+). pM41Struct was digested with PacI and BspHI and the PacI-BspHI fragment was purified and retained (FIG. 3). A Beaudette-CK/M41-CK chimaeric S gene, consisting of the signal sequence, ectodomain and transmembrane regions derived from M41-CK and the cytoplasmic tail domain from Beau-R, was generated. The M41-CK-derived PadcI-BspHI fragment from pM41Struct was used to replace the corresponding Beaudette-CK-derived cDNA PacI-BspHI sequence in pFRAG-3. A three way ligation reaction between the PacI-SalI vector-containing fragment (from pFRAG-3), the M41-CK-derived PacI-BspHI S gene fragment and the BspHI-SalI fragment corresponding to the rest of the Beaudette genome downstream of the S gene, was performed resulting in pACNR-NheI-NotI-IBV-M41-S (FIG. 4 and summarised in FIG. 5A). Sequence analysis of pFRAG3-M41S confirmed the presence of a contiguous chimaeric S gene sequence, along with the presence of the two marker mutations, $U^{18668}$ and $G^{27087}$, originally present in pFRAG3.

IBV-derived cDNA fragments from pFRAG-3-M41S, containing the chimaeric S gene sequence, and pFRAG-1 and pFRAG-2 were used to generate a full-length IBV cDNA using in vitro ligation. The full-length cDNA was generated using a two-step in vitro ligation procedure as described by Casais et al. (2001, supra). In the first step, the SacI-NheI cDNA (FRAG-2) from pFRAG-2 and the NheI-BspHI cDNA (FRAG-3-M41S) from p FRAG-3-M41S were ligated to give a 21.5 kb SacI-Bsp120I fragment that was gel purified. In the second step, the 21.5 kb SacI-Bsp120I fragment was ligated to BspHI-SacI cDNA (FRAG-1) from pFRAG-1 to produce a 27.9 kb full-length IBV cDNA (FIG. 5B). This full-length cDNA, containing the chimaeric S gene, was under the control of a T7 RNA polymerase promoter and terminated by a HδR-T7 termination sequence distal to poly (A). The T7 promoter and HδR-T7 termination sequence were required for the in situ generation of infectious IBV RNA by T7 RNA polymerase. The products from the second in vitro ligation, containing the full-length IBV cDNA with dephosphorylated Bsp120I ends, were directly ligated to vNotI/tk NotI-derived arms in the presence of NotI. The ligation products were used without further purification to recover recombinant vaccinia viruses using fowlpox virus helper vines, FP9, in CV-1 cells. We obtained 22 recombinant vaccinia viruses and restriction analysis of the DNA isolated from infected cells indicated that eight of them contained an insert of the expected size of which vNotI/IBV$_{FL}$-M41S, was selected for further analysis Recombinant IBV Beaudette-4/91 Spike Gene Sequence analysis of the 4/91 S gene identified 562 nt differences when compared to the BeauR S gene sequence of which 245 represented non-synonymous and 317 synonymous substitutions resulting in a total of 201 amino acid differences between the two S glycoproteins of which two resulted from a six nucleotide insertion within the 4/91 S gene sequence. There are two amino acid differences between the cytoplasmic domains of the two viruses. Overall, the primary translation products of the two S genes are 1162 and 1164 amino acids for Beau-R and 4-91, respectively, with an identity of 83% between the two S proteins. The region of the S gene containing the overlapping region of the replicase gene was acquired from 4/91 for generation of the rIBV S gene sequence. In addition, because the C-terminal ends of the Beaudette and 4/91 S genes are similar, we retained the last 137 nt of the Beaudette S gene, identical to the 4/91 sequence for assembly of the chimaeric S gene. The resulting S protein from the chimaeric S gene sequences consists of the ectodomain from 4/91, the transmembrane domain from 4/91 and the cytoplasmic tail domain from Beaudette-CK and is analogous to the chimaeric M41 S protein described above.

Figure 6:
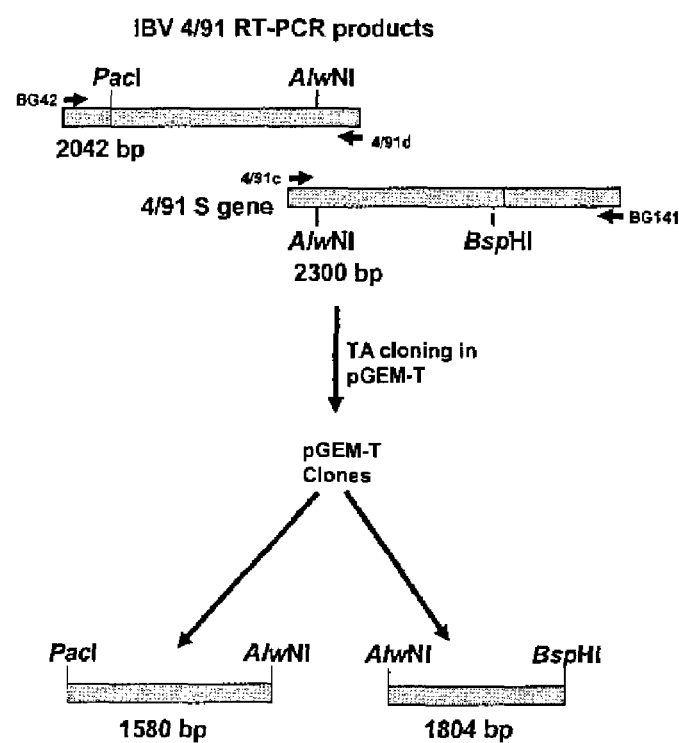
FIG. 6. Schematic diagram for the isolation of PCR products representing the 4/91 S gene sequence.

The 4/91 S gene sequence was obtained from virus-derived RNA isolated form the virulent 4/91 IBV strain using two PCRs. The two PCR products, 2042 bp and 2300 bp, were generated using two sets of oligonucleotides (FIG. 6). The 2042 bp product was generated using oligonucleotide BG42 (corresponding to nucleotides 19941-19958 on the Beau-R genome) and a specific 4/91 oligonucleotide, 4/91d (the reverse complement to the equivalent nucleotides 21957-21976 on the Beau-R genome). The 2300 bp product was generated using a specific 4/91 oligonucleotide 4/91c (corresponding to the equivalent nucleotides 21600-21619 on the Beau-R genome) and oligonucleotide BG141 (the reverse complement of nucleotides 23879-23898 on the Beau-R genome). Both fragments were inserted into pGEM-T and the resulting plasmids were used as the source of the 4/91 S gene sequence (FIG. 6).

The chimaeric 4/91 S gene sequence was constructed by modifying pGPT-M41S (FIG. 7A) using the two 4/91-derived PCR products. The 2042 bp 4/91-derived product in pGEM-T was excised as a 1580 bp fragment, representing the 5' half of the 4/91 S gene, using PacI and AlwNI which was purified and retained (FIG. 6). The 2300 bp 4/91-derived product in pGEM-T was excised as a 1804 bp fragment, representing the 3' half of the 4/91 S gene, using AlwNI and BspHI which was purified and retained (FIG. 6). Plasmid pGPT-M41S was digested with PacI and BamHI and the 5018 bp fragment representing the plasmid sequence was purified and retained (FIG. 7A). In addition, pGPT-M41S was digested with BspHI and BamHI and a BeauR-derived 1080 bp fragment was purified and retained (FIG. 3A). A four-way ligation reaction between the 5018 bp PacI-BamHI plasmid-containing fragment, the 1080 bp BspHI-BamHI Beau-R-derived fragment, the 1580 bp PacI-AlwNI 4/91-derived fragment and the 1804 bp AlwNI-BspHI 4/91-derived fragment was performed resulting in pGPT-4/91S (FIG. 7B). This resulted in the construction of a 4/91-Beau-CK chimaeric S gene sequence, consisting of the signal sequence, ectodomain and transmembrane regions derived from 4/91 and the cytoplasmic tail domain from Beau-R (FIG. 7B). Sequence analysis of pGPT-4/91S confirmed the presence of a contiguous chimaeric S gene sequence.

Figure 8:
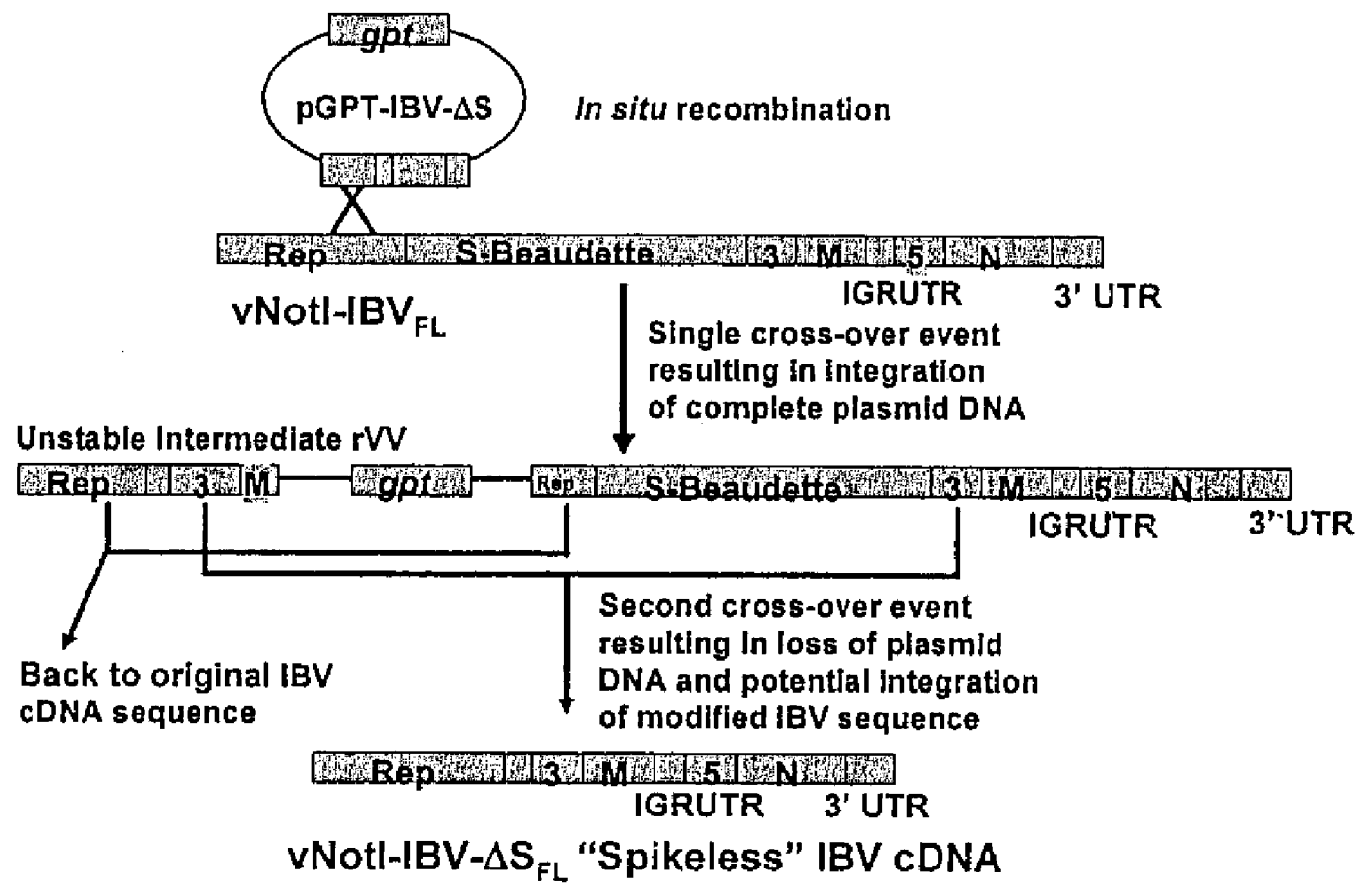
Figure 9:
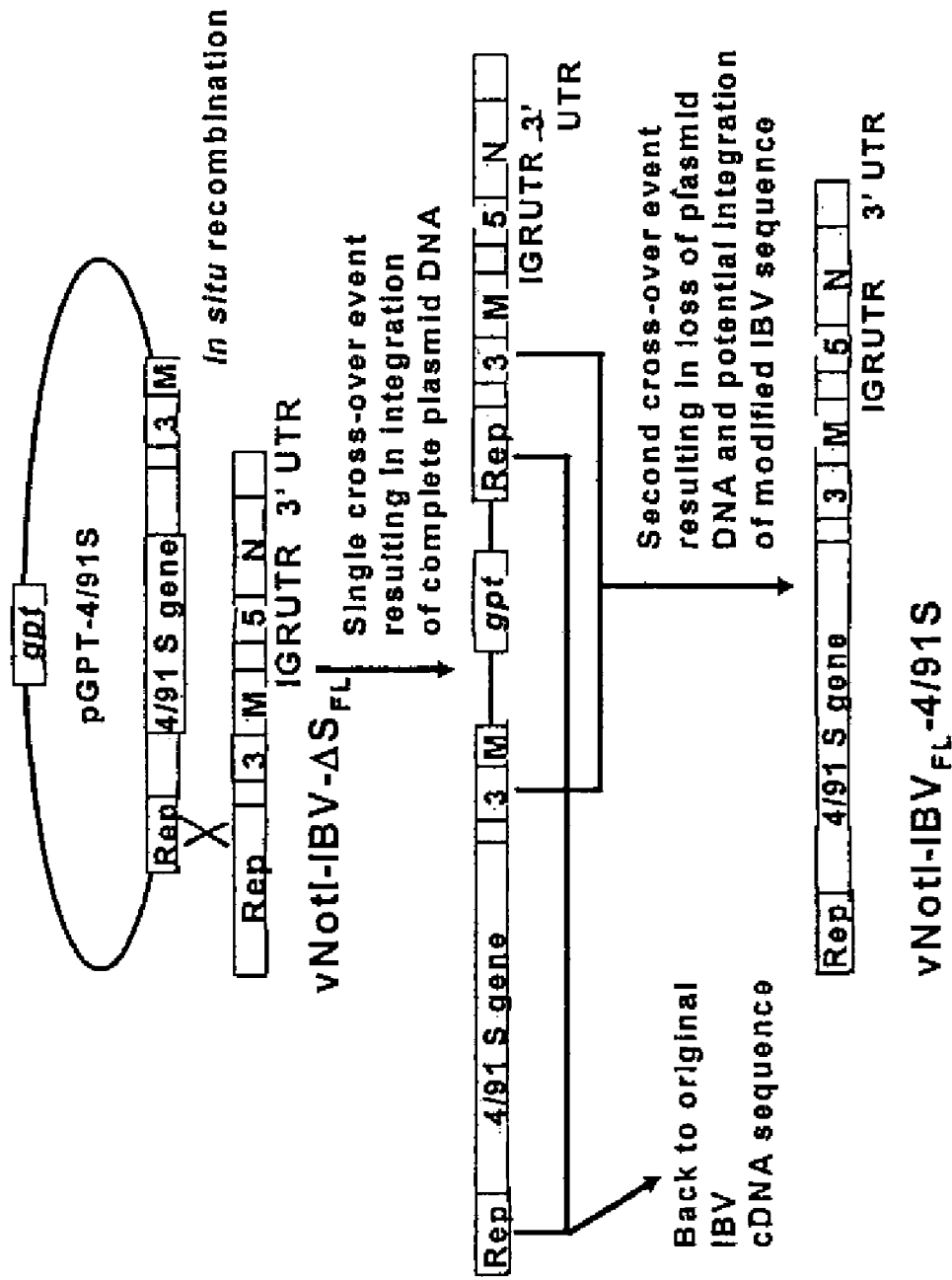

In order to modify the Beaudette CK-derived full length cDNA in recombinant vaccinia virus vNotI/IBV$_{FL}$ we used the transient dominant selection (TDS) method (Falkner and Moss, Journal of Virology 64, 3108-3111, 1990) to replace the Beaudette S gene sequence with the 4/91-Beau-CK chimaeric S gene sequence. The TDS system consisted of a two step process (FIGS. 8 and 9). In the first step the TDS method was used to remove the Beaudette S gene sequence from the full length cDNA in recombinant vaccinia virus vNotI/IBV$_{FL}$. Plasmid pGPT-IBV-ΔS, containing Beau-CK sequence corresponding to the replicase and gene 3 with part of the M gene, but lacking the S gene sequence was transfected into cells infected with vNotI/IBV$_{FL}$. Following homologous recombination between IBV-derived sequence in pGPT-IBV-ΔS and the IBV sequence within vNotI/IBV$_{FL}$ a recombinant vaccinia virus, vNotI/IBV-ΔS$_{FL}$, containing the IBV cDNA lacking the S gene sequence ("spikeless" recombinant) was isolated and identified (FIG. 8). In the second step the TDS method was used to insert the 4/91-Beau-CK chimaeric S gene sequence into the "spikeless" recombinant vaccinia virus vNotI/IBV-ΔS$_{FL}$. Plasmid pGPT-4/91S was transfected into cells infected with vNotI/IBV-ΔS$_{FL}$ and following recombination IBV-derived sequence in pGPT-4/91S and the IBV sequence within vNotI/IBV-ΔS$_{FL}$ a recombinant vaccinia virus, vNotI/IBV$_{FL}$-4/91S containing the full-length IBV cDNA with the 4/91-Beau-CK chimaeric S gene sequence inserted was isolated and identified (FIG. 9).

Recovery of Infectious IBVs Expressing the Beaudette-M41 and Beaudette-4/91 Chimaeric Spike Protein.

Infectious rIBV was recovered from vNotI/IBV$_{FL}$-M4/19S or vNotI/IBV$_{FL}$-4/91S using CK cells, previously infected with rFPV/T7 (Britton et al., J. Gen. Virol. 77, 963-967, 1996), to provide T7 RNA polymerase, and co-transfected with AscI-restricted vNotI/IBV$_{FL}$-M41S DNA or vNotI/IBV$_{FL}$-4/91S and pCI-Nuc (Hiscox et al., J. Virol. 75, 506-512, 2001). The vNotI/IBV$_{FL}$-M41S or vNotI/IBV$_{FL}$-4/91S DNA was prepared from semi-purified vaccinia virus and pCi-Nuc, a plasmid expressing the IBV N protein under control of both the T7 and CMV promoters was required for the successful recovery of rIBV.

The transfected CK cells (P$_0$) were incubated until they showed a cytopathic effect (CPE), the medium was filtered to removed any rFPV/T7 and any potential IBV passaged on fresh CK cells (P$_1$). A rIBV, BeauR-M41(S), was isolated from the P$_1$ cells and the genotype of the rIBV determined by sequence analysis. Which confirmed the presence of the two marker mutations and that the ectodomain of the chimaeric S protein gene was derived from the M41-CK S gene sequence. BeauR-M41(S), derived from P$_5$ CK cells, was used for further characterisation.

Example 2

Biological Characterization of Recombinant BeaudetteR -M41 Spike IBV In-Vitro

Viral Growth Curves.

Confluent monolayers of CK, Vero, CEF and BHK-21 cells in 60 mm dishes were infected with 1.5×10$^6$ PFU of IBV. Following adsorption, for 1 h at 37° C., the cells were washed three times with phosphate-buffered saline (PBS) to remove residual virus and incubated at 37° C. in 5 ml of the appropriate media. Samples of media were, at selected times over a 96 h period, analyzed in triplicate for progeny virus by plaque assay.

Replication of BeauR-M41(S) in Different Cell Lines.

IBV strains Beau-CK and M41-CK have differing cell tropism. It is known that both viruses replicate to similar titres in CK cells but only Beau-CK produces infectious virus on Vero cells. Therefore by using the recombinant isogenic viruses, BeauR and BeauR-M41(S), that differ only in the ectodomain of the S protein, we sought to determine whether the IBV S glycoprotein was responsible for the observed differences in the ability of distinct IBV strains to infect and replicate in different cell lines.

Figure 10:
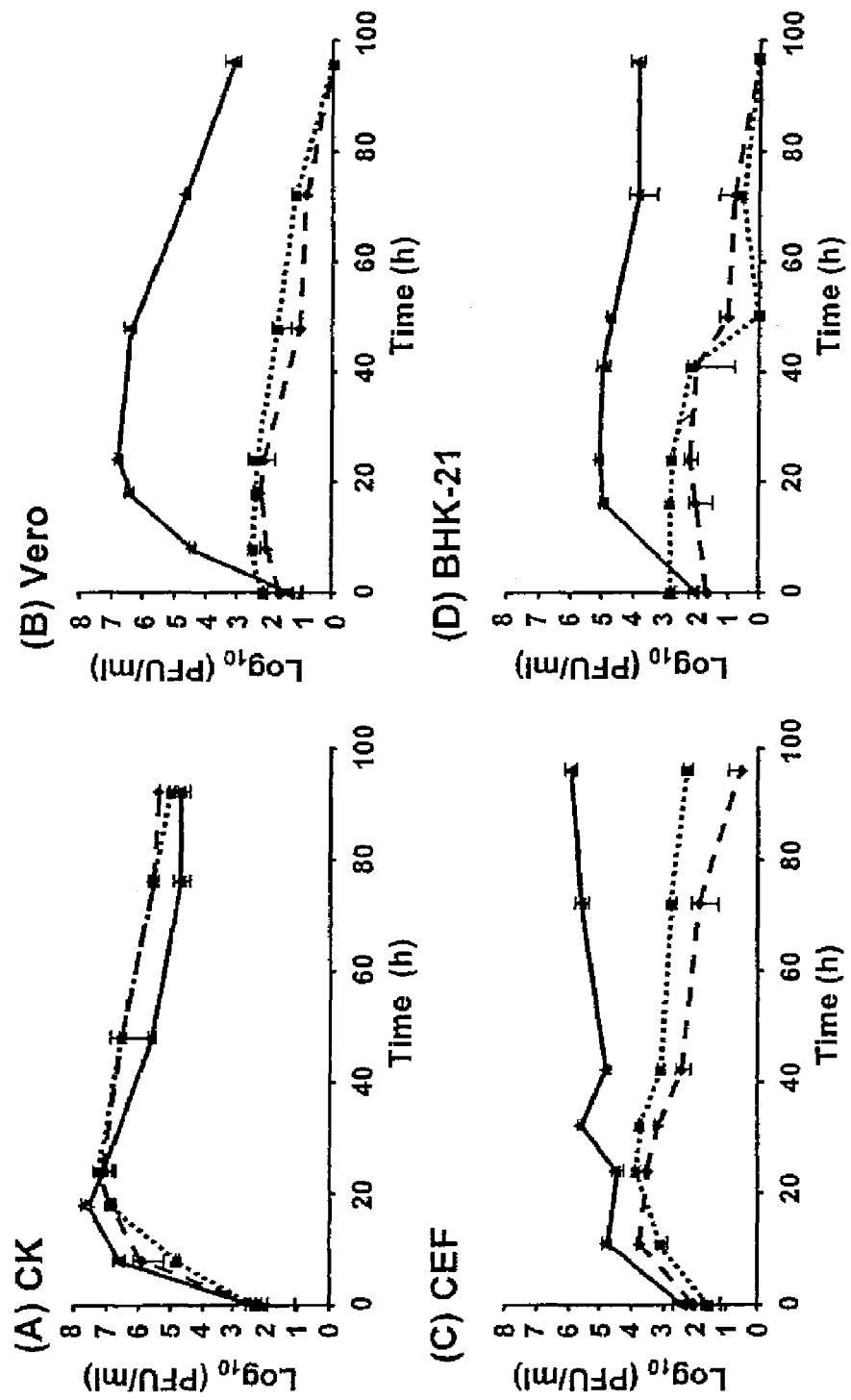

BeauR, M41-CK and BeauR-M41(S), displayed similar growth profiles on CK cells (FIG. 10 A). In addition, all three viruses caused CPE within 24 h. Analysis of the growth profiles of the three viruses in Vero, CEF and BHK-21 (FIG. 10 B-D) showed that only Beau-R replicated to any significant extent in the different cells, usually with maximum titre by 24 h postinfection. These results showed that BeauR-M41 (S) had the same tropism as M41-CK on all four cell types, indicating that replacement of the ectodomain of the Beaudette S glycoprotein with the corresponding sequence from the M41-CK S glycoprotein resulted in a rIBV with an altered cell tropism when compared to BeauR.

Results from analyses of RT-PCR products from RNA isolated from cells infected with these viruses and indirect immunofluorescence analysis of IBV infected cells corroborated with the growth experiment results.

Example 3

Biological Characterization of Recombinant BeaudetteR -M41 Spike IBV In-Vivo (Post-Hatch Administration)

A Safety of Recombinant IBVs (rIBVs) BeauR and BeauR-M41(S)

Materials and Methods

Viruses and Cells

The Massachusetts M41-CK strain of IBV, virulent for hatched chickens, was used after 11 passages in primary chick kidney (CK) cells and three passages in 10-day-old embryos of specified pathogen free (SPF) Rhode Island Red (RIR) chickens. The rIBVs BeauR and BeauR-M41(S) were propagated in CK cells. The viruses were titrated in chick embryo tracheal organ cultures. Titres were expressed in $\log_{10}$ ciliostatic dose 50.

Chickens

Eight-day-old RIR chickens were inoculated by eye-drop and in the nose with 0.1 ml of phosphate buffered saline containing 3.0 $\log_{10}$ ciliostatic dose 50 of virus, or with PBS alone (mock-inoculated group). The birds were housed in groups.

Animal Study

To determine if either of the two rIBVs were pathogenic in hatched chickens, three clinical signs were recorded: snicking, nasal discharge and rales. Snicking was recorded for groups of birds during a two-minute period and is presented as snicks/bird/minute. Nasal discharge (clear or turbid) and rales (moderate and severe) were recorded for birds individually, the incidence being presented below as a percentage of the group. Ciliary activity was determined by killing the birds, removing the trachea, slicing the trachea transversely into rings approximately 1 mm deep and observing them by low power microscopy. 10 rings were examined for each trachea. Ciliary activity was recorded as being approximately 100%, 75%, 50%, 25% or 0%. Groups comprised not less than 20 birds on the days when the data below was recorded.

Results

Snicking was maximal on day 6 p.i. There was no significant difference in the rate of snicking of BeauR- and BeauR-M41(S)-infected birds and the mock-infected birds. The M41-CK strain induced an order of magnitude more snicking (table 1).

TABLE 1

| Inoculum | Snicks/bird/minute on day 6 p.i. |
| --- | --- |
| Mock | 0.07 |
| BeauR | 0.14 |
| BeauR-M41(S) | 0.24 |
| M41-CK | 2,51 |

Nasal discharge was maximal on day 5 p.i. The M41-CK-infected birds exhibited nasal discharge in a majority of birds whereas the two recombinant viruses did so in only a few birds. There was no statistically significant difference between the numbers of birds exhibiting nasal discharge in the mock-infected and rIBV-infected groups (table 2).

TABLE 2

| Inoculum | Birds with nasal discharge on day 5 p.i. (%) |
| --- | --- |
| Mock | 0 |
| BeauR | 4 |
| BeauR-M41(S) | 12 |
| M41-CK | 75 |

Rales were maximal on day 4 p.i. in the M41-CK-infected group. BeauR-M41(S) and BeauR did not cause any moderate or severe rales (table 3)

TABLE 3

| Inoculum | Birds exhibiting moderate or severe rales on day 4 p.i. (%) |
| --- | --- |
| Mock | 0 |
| BeauR | 0 |
| BeauR-M41(S) | 0 |
| M41-CK | 41 |

Neither of the rIBVs diminished ciliary activity, whereas the virulent M41-CK caused complete ciliostasis (table 4).

TABLE 4

| Inoculum | Mean ciliary activity of tracheal rings on day 5 p.i. (%) |
| --- | --- |
| Mock | >90 |
| BeauR | >90 |
| BeauR-M41(S) | >90 |
| M41-CK | 0 |

The results depicted in the Tables above demonstrate that both the parent IBV BeauR and the swap mutant BeauR-M41 (S) were not pathogenic for newly hatched chickens.

B Efficacy of Induction of Protective Immunity by BeauR and BeauR-M41(S)

Materials and Methods

Animal Study

The birds in this Experiment which had been vaccinated with BeauR, BeauR-M41(S), M41-CK or no virus at eight days of age, were challenged 21 days later with 3 $\log_{10}$ ciliostatic does 50 of virulent IBV M41-K A fifth group of birds had been mock-infected. This was retained as a non-challenged group. Four days after challenge of the chicks, tracheas were removed, the epithelium was scraped off and resuspended in 1 ml of medium. This was titrated in tracheal organ cultures, and the titre expressed as log 10 ciliostatic dose 50 ($CD_{50}$).

Results

Challenge, with virulent M41-CK, of birds that had been vaccinated with BeauR-M41(S) resulted in snicking at a low level, similar to that of the birds that had been both vaccinated and challenged with M41-CK. In contrast BeauR-vaccinated birds exhibited a high rate of snicking, although less than the non-vaccinated birds that were challenged (table 5).

TABLE 5

| First inoculum (vaccination) | Snicks/bird/minute on day 5 after challenge with virulent IBV M41-CK |
|---|---|
| Mock | 0.96 |
| BeauR | 0.60 |
| BeauR-M41(S) | 0.18 |
| M41-CK | 0.11 |
| Mock | (not challenged) 0.06 |

Challenge with M41-CK caused nasal discharge in 56% of the mock-vaccinated birds and no nasal discharge in birds that had been vaccinated with BeauR-M41(S) or M41-CK (table 6).

TABLE 6

| First inoculum (vaccination) | Birds with nasal discharge on day 5 after challenge with virulent IBV M41-CK (%) |
|---|---|
| Mock | 56 |
| BeauR | 6 |
| BeauR-M41(S) | 0 |
| M41-CK | 0 |
| Mock | (not challenged) 0 |

Challenge with M41-CK caused moderate or severe rales in 23% of mock-vaccinated bids on day 6 p.i. and in none of the birds that had been vaccinated with the rIBVs (table 7)

TABLE 7

| First inoculum (vaccination) | Birds exhibiting moderate or severe rales on day 6 after challenge with virulent IBV M41-CK (%) |
|---|---|
| Mock | 23 |
| BeauR | 0 |
| BeauR-M41(S) | 0 |
| M41-CK | 0 |
| Mock | (not challenged) 0 |

Birds that had been vaccinated with M41-CK were fully protected against challenge with M41-CK; ciliary activity was 100%, in contrast to non-vaccinated birds, where there was no ciliary activity. Most (7/9) of the birds that had been vaccinated with BeauR-M41(S) had high ciliary activity (>50%) after challenge i.e. they had resisted the challenge. The remaining two birds had almost 50% activity (table 8).

TABLE 8

| First inoculum (vaccination) | Birds with ≧50% tracheal ciliary activity on days 4, 5 and 6 after challenge with virulent IBV M41-CK | |
|---|---|---|
| | number/total number | % |
| Mock | 0/6 | 0 |
| BeauR | [1]1/9 | 11 |
| BeauR-M41(S) | [2]7/9 | 77 |
| M41-CK | 6/6 | 100 |
| Mock | (not challenged) 6/6 | 100 |

[1]The other 8 birds in this group had <25% ciliary activity.
[2]The other 2 birds in this group had 48% and 45% ciliary activity.

No challenge virus could be detected in the various groups of vaccinated birds (table 9).

TABLE 9

| First inoculum (vaccination) | Detection of challenge virus (IBV M41-CK) in the trachea at 4 days after challenge |
|---|---|
| Mock | +[a] |
| BeauR | −[b] |
| BeauR-M41(S) | −[b] |
| M41-CK | −[b] |

[a]Mean titre of recovered challenge virus was 2.9 $log10_{50}$/ml.
[b]No challenge virus recovered.

These challenge experiments demonstrate that BeauR-M41(S) is able to induce protection against challenge to an extent similar to M41-CK, whereas the parent IBV BeauR only induces a poor protection.

Example 4

Biological Characterization of Recombinant Beaudette—M41 Spike IBV In-Vivo (In Ovo Administration)

Trial 1 Safety and Efficacy Study for In-Ovo Vaccination with IBV

Hatchability

Groups of specific pathogen free (SPF) eggs were incubated until 18 days of embryonation. The in-ovo vaccinations given are summarized in table 10. One dose of Ma5, a Massachusetts serotype IBV vaccine (Intervet International BV), was given to group 1, group 2 was not vaccinated, group 3 received the IBV swap mutant Beau-R-M41(S) and group 4 the recombinant Beau-R The viruses were diluted in Modified Eagles medium (MEM). A small hole was drilled in the egg above the air-space and an inch long, 20 gauge needle used to release 0.1 ml of the virus into the amniotic fluid. The eggs were placed in separate incubators and hatchability was assessed on day 21 of incubation

TABLE 10

| Group | Inoculation | Dose ($EID_{50}$) by back-titration | Number of eggs | Hatchability % |
|---|---|---|---|---|
| 1 | 1 dose Ma5 | 4.4 | 33 | 18 |
| 2 | none | — | 33 | 65 |
| 3 | Beau-R-M41(S) | ≧6.2 | 33 | 82 |
| 4 | Beau-R | ≧5.9 | 33 | 73 |

Assessment of Clinical Signs Post Hatch

On day 6 post hatch the birds were assessed for nasal exudate (NE), a clinical sign associated with IBV infection. NE was not detected in birds vaccinated in-ovo with Beau-R or BeauR-M41(S). However, NE was detected in a proportion of the Ma5 in-ovo vaccinates that had hatched (Table 11).

TABLE 11

| Group number | Treatment | Dose ($EID_{50}$) | Signs/no of birds | Percentage |
|---|---|---|---|---|
| 1 | 1 dose Ma5 | 4.4 | 4/6 | 67 |
| 2 | Control | — | 0/25 | 0 |
| 3 | Beau-R-M41 | $\geq 6.2$ | 0/26 | 0 |
| 4 | Beau-R | $\geq 5.9$ | 0/23 | 0 |

To further assess the effect of the IBV vaccinations in-ovo a small number of birds were euthanased on day 7 so that an assessment of the tracheal ciliary activity could be made. Ciliary activity is used as a measure of the attenuation of the inoculated IBV. Tracheas from inoculated birds/embryos are cut into 10 sections, 3 from the top and bottom, and four from the middle. A microscopic assessment of ciliary activity is made and the mean percentage cilia that have stopped beating for the 10 rings is calculated. The higher the score the more the IBV-induced damage.

Ma5 inoculated in-ovo, although only assessed in 1 bird, gave very high ciliostasis scores in each bird (table 12). Both of the recombinant IBV Beaudette gave low scores that are acceptable on the grounds of safety.

TABLE 12

| Group number | Treatment | Dose ($EID_{50}$) | Mean percentage ciliostasis |
|---|---|---|---|
| 1 | 1 dose Ma5 | 4.4 | 90 |
| 2 | Control | — | 2.5 |
| 3 | Beau-R-M41(S) | $\geq 6.2$ | 24 |
| 4 | Beau-R | $\geq 5.9$ | 29.5 |

Virulent IBV Challenge,

To determine the efficacy of in-ovo vaccination with the infectious clones 4 weeks post hatch, a selection of birds were challenged with 2.9 log 10 $EID_{50}$ of virulent Massachusetts serotype IBV M41 by the ocular-nasal route. On days 5 and 7 post challenge ciliostasis tests were performed on tracheal rings of euthanased birds. Based on an individual ciliostasis score of 50% or less being protected, 100% of the Ma5 vaccinated birds were protected, 90% of the BeauR-M41(S) birds were protected and 30% of the Beau-R vaccinated birds were protected. The individual and mean ciliostasis scores are shown in table 13.

Trial 2 Safety Study for In-Ovo Vaccination with IBV

In a second trial the hatchability following in-ovo vaccination was reassessed. As described for trial 1 the eggs (40/group) were vaccinated at 18 days of embryonation with either of the infectious clones or with a placebo (MEM). The ciliostasis test was performed on days 2, 5, 8 and 12 days post hatch to confirm the safety of the vaccination. It is shown that vaccination with BeauR-M41(S) has a minimal effect on hatchability and causes minimal tracheal damage.

TABLE 14

| Group | Virus at 18 day embryonation | % hatch |
|---|---|---|
| 1 | Beau-R | 67 |
| 2 | Beau-R-M41(S) | 75 |
| 3 | Placebo | 82 |

TABLE 15

| Group | Inoculum | Mean % ciliostasis score 2 days old | Mean % ciliostasis score 5 days old | Mean % ciliostasis score 8 days old | Mean % ciliostasis score 12 days old |
|---|---|---|---|---|---|
| 1 | Beau-R | 32 | 42 | 24 | 23 |
| 2 | Beau-R-M41(S) | 33.5 | 37.5 | 36 | 24 |
| 3 | Placebo | 19.5 | 10.5 | 14.5 | 12 |

LEGENDS TO THE FIGURES

FIG. 1. Schematic diagram of the IBV S gene. The 5' end of the S gene overlaps the 3' end of the replicase gene. The four domains of the S protein, the position of the S1/S2 cleavage point and the positions of the PacI and BspHI restriction sites, the S gene TAS, the gene 3 TAS and the start of gone 3 are shown. The numbers refer to the positions of the amino acid differences between IBV Beaudette-CK and M41-CK-S protein sequences within the chimaeric S gene sequences, resulting from non-synonymous substitutions following exchange of the two S gene sequences.

Figure 2:
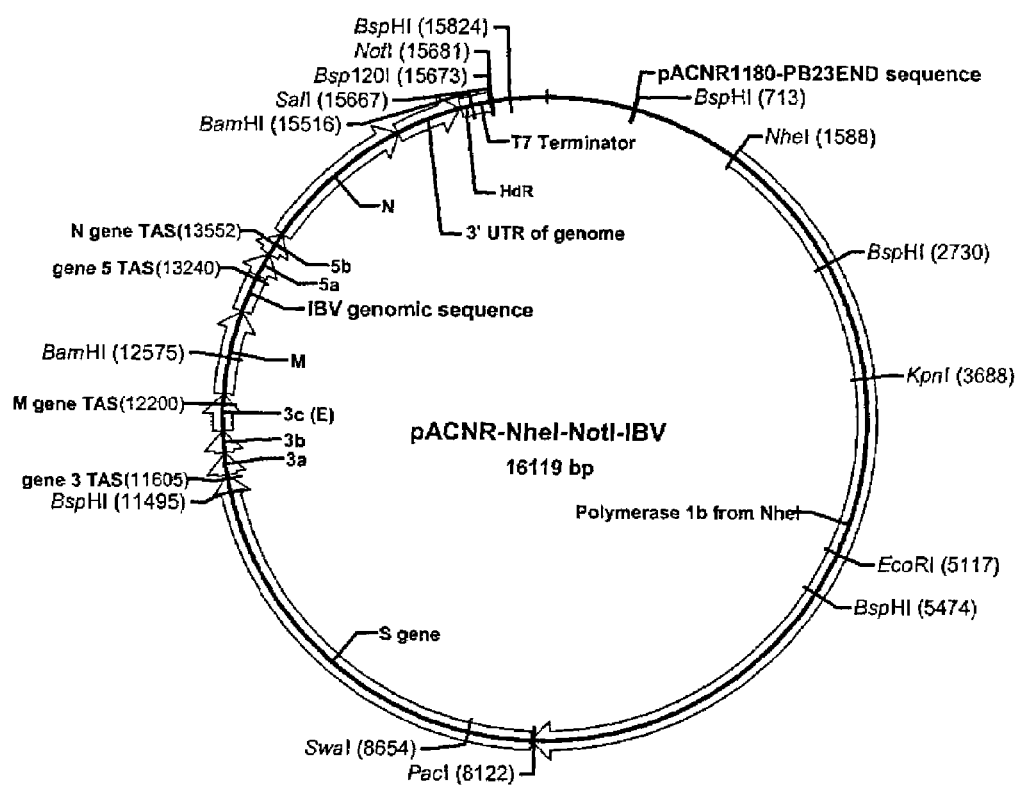
FIG. 2. Schematic structure of plasmid pACNR-NheI-NotI-IBV used as a source of FRAG-3 for the generation of full-length Beaudette-CK derived full-length cDNAs. The plasmid was used for removal of the region of the Beaudette-CK gene encoding the signal sequence, ectodomain and transmembrane domain. Restriction sites are indicated.

FIG. 2. Schematic structure of plasmid pACNR-NheI-NotI-IBV used as a source of FRAG-3 for the generation of full-length Beaudette-CK derived full-length cDNAs. The plasmid was used for removal of the region of the Beaudette-CK gene encoding the signal sequence, ectodomain and transmembrane domain. Restriction sites are indicated.

FIG. 3. Schematic structure of the 3383 bp PacI-BspHI cDNA fragment comprising the signal sequence, ectodomain and transmembrane domain of the M41 spike gene. Restriction sites are indicated.

TABLE 13

| Group number | Treatment | Individual percentage ciliostasis scores day 5 post challenge | Group Mean | Individual percentage ciliostasis scores day 7 post challenge | Group Mean | % protection |
|---|---|---|---|---|---|---|
| 1 (n = 4), | 1 dose Ma5 | 15, 15 | 15 | 42.5, 32.5 | 37.5 | 100 |
| 2 (n = 10) | Control | 97.5, 100, 100, 100, 100 | 99.5 | 100, 97.5, 97.5, 95, 97.5 | 97.5 | 0 |
| 3 (n = 10) | Beau-R-M41 | 7.5, 80, 12.5, 10, 17.5 | 25.5 | 22.5, 32.5, 27.5, 20, 30 | 26.5 | 90 |
| 4 (n = 10) | Beau-R | 100, 95, 95, 97.5, 95 | 96.5 | 67.5, 40, 27.5, 62.5, 40 | 47.5 | 30 |

FIG. 4. Schematic structure of plasmid pACNR-NheI-NotI-IBV-M41-S comprising the chimaeric S gene and used as the source of FRAG-3-M41S for generation of an IBV full-length cDNA containing the chimaeric S gene sequences. Restriction sites are indicated.

FIG. 5. Schematic diagram for the construction of the chimaeric S gene and production of a full-length IBV cDNA. (A) Replacement of the signal sequences, ectodomain and transmembrane regions of the Beaudette-CK S gene with the corresponding sequence from IBV M41-CK for construction of FRAG-3-M41S. (B) Schematic diagram of the BeauR-M41(S) full-length cDNA composed of FRAG-1, FRAG-2 and FRAG-3-M41S.

FIG. 6. Schematic diagram for the isolation of PCR products representing the 4/91 S gene sequence.

Figure 7:
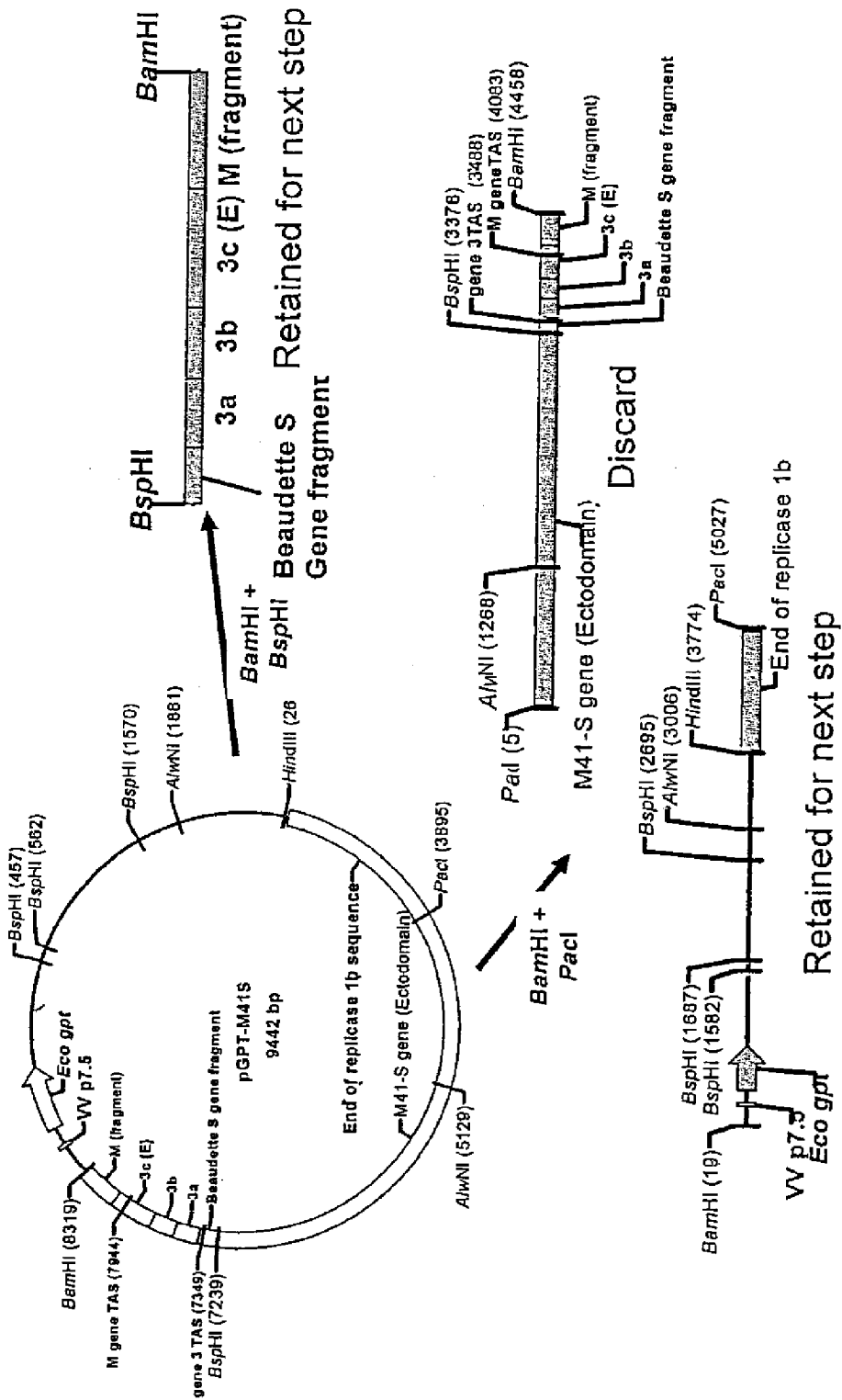
Figure 7:
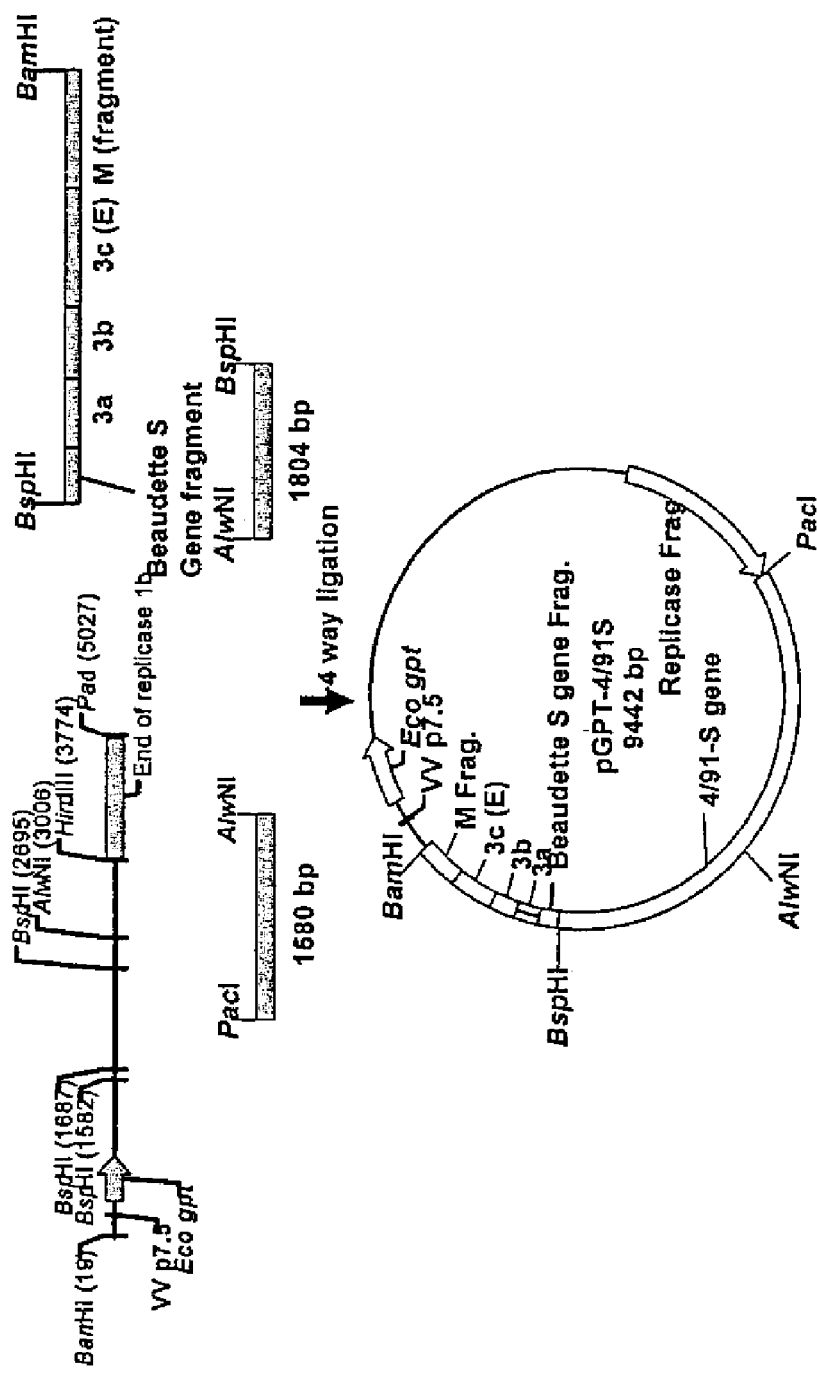

FIG. 7. Schematic diagram showing assembly of the chimaeric 4/91 S gene in pGPT-4/91S. (A) Two fragments were generated from pGPT-M41S for use in the assembly process. A fragment representing the chimaeric M41 S gene was discarded. (B) Assembly of the chimaeric 4/91 S gene in pGPT-4/91S, by a four-way ligation reaction, using the two fragments isolated from pGPT-M41S in conjunction with the two digestion products representing the 4/91 S gene sequence. The relevant fragments and restriction sites are indicated.

FIG. 8. Schematic representation of the first TDS step for generating the "spikeless" IBV cDNA within recombinant vaccinia virus vNotI-IBV-$\Delta S_{FL}$.

FIG. 9. Schematic representation of the second TDS step for insertion of the 4/91-Beau-R chimaeric S gene into the full-length IBV cDNA within the recombinant vaccinia virus vNot-IBVFL-4/91S.

FIG. 10. Growth profiles of the three IBVs on four cell types. The panels show the growth pattern of Beau-R (solid line with triangle), M41-CK (dashed line with diamond) and BeauR-M41(S) (dotted line with square) on (A) CK cells, (B) Vero cells, (C) CEF cells and (D) BHK-21 cells.

The invention claimed is:

1. A vaccine composition effective for protecting poultry against infectious bronchitis, comprising an immunogenically effective amount of attenuated infectious bronchitis virus (IBV) and a pharmaceutically, acceptable carrier or diluent, wherein the attenuated IBV is IBV strain Beaudette that comprises a heterologous IBV spike protein gene.

2. The vaccine composition according to claim 1, wherein the heterologous spike gene encodes a spike protein of an IBV of Massachusetts serotype.

3. The vaccine composition according to claim 2, wherein the heterologous spike gene encodes a spike protein of IBV strain M41.

4. The vaccine composition according to claim 1 wherein the heterologous spike gene encodes a spike protein of an IBV 793B serotype.

5. The vaccine composition according to claim 1, wherein the heterologous spike gene replaces the original spike gene.

6. The vaccine composition according to claim 1, wherein the IBV is in a live form.

7. The vaccine composition according to claim 1, further comprising at least one vaccine strain of another pathogen infectious to poultry.

8. The vaccine according to claim 1, wherein the vaccine comprises an adjuvant.

9. A method for the protection of poultry against infectious bronchitis, comprising administering an immunogenically effective amount of a vaccine composition comprising IBV Beaudette strain BeauR that comprises a heterologous IBV spike gene to the poultry via the in ovo route.

10. The vaccine composition of claim 4, wherein the heterologous spike gene encodes a spike protein of IBV strain 4/91.

* * * * *

SEQUENCE LISTING

```
<160> NUMBER OF SEQ ID NOS: 2

<210> SEQ ID NO 1
<211> LENGTH: 3498
<212> TYPE: DNA
<213> ORGANISM: Infectious bronchitis virus
<220> FEATURE:
<221> NAME/KEY: CDS
<222> LOCATION: (1)..(3492)
<220> FEATURE:
<221> NAME/KEY: sig_peptide
<222> LOCATION: (1)..(54)
<220> FEATURE:
<221> NAME/KEY: mat_peptide
<222> LOCATION: (55)..(3492)
<220> FEATURE:
<221> NAME/KEY: misc_structure
<222> LOCATION: (55)..(3279)
<223> OTHER INFORMATION: Ectodomain
<220> FEATURE:
<221> NAME/KEY: misc_feature
<222> LOCATION: (1603)..(1617)
<223> OTHER INFORMATION: S1 / S2 cleavage site
<220> FEATURE:
<221> NAME/KEY: misc_structure
<222> LOCATION: (3280)..(3363)
<223> OTHER INFORMATION: Transmembrane domain
<220> FEATURE:
<221> NAME/KEY: misc_feature
<222> LOCATION: (3353)..(3358)
<223> OTHER INFORMATION: BspH I restriction site
<220> FEATURE:
<221> NAME/KEY: misc_structure
<222> LOCATION: (3364)..(3492)
<223> OTHER INFORMATION: Cytoplasmic tail domain

<400> SEQUENCE: 1 atg ttg ggc aaa ccg ctt tta cta gtg act ctt tgg tat gca cta tgt        48
Met Leu Gly Lys Pro Leu Leu Leu Val Thr Leu Trp Tyr Ala Leu Cys
            -15                 -10                 -5 agt gct ttg ctt tat gat aaa aat act tac gtt tac tac tac caa agt        96
Ser Ala Leu Leu Tyr Asp Lys Asn Thr Tyr Val Tyr Tyr Tyr Gln Ser
     -1   1                   5                  10 gcc ttt agg cct ggt caa ggt tgg cat cta cat ggg gtt gct tat gca       144
Ala Phe Arg Pro Gly Gln Gly Trp His Leu His Gly Gly Ala Tyr Ala
 15                  20                  25                  30 gta gat aag gtt ttt aat gga acc aac aat gca gtc agt gta tct gat       192
Val Asp Lys Val Phe Asn Gly Thr Asn Asn Ala Val Ser Val Ser Asp
```

```
                35                    40                    45 tgc act gct ggt act ttt tat gaa agc tat aat att tct gct gct tct        240
Cys Thr Ala Gly Thr Phe Tyr Glu Ser Tyr Asn Ile Ser Ala Ala Ser
             50                      55                      60 gta gcc atg aca gta cca cct gct ggt atg tct tgg tca gtt tca cag        288
Val Ala Met Thr Val Pro Pro Ala Gly Met Ser Trp Ser Val Ser Gln
         65                      70                      75 ttt tgt aca gct cat tgt aac ttc tca gac ttt aca gtg ttt gtt acg        336
Phe Cys Thr Ala His Cys Asn Phe Ser Asp Phe Thr Val Phe Val Thr
     80                      85                      90 cat tgt ttt aaa agt caa caa ggt agt tgt cca ttg aca ggt atg att        384
His Cys Phe Lys Ser Gln Gln Gly Ser Cys Pro Leu Thr Gly Met Ile
 95                     100                     105                 110 cct cag aat cat att cgt att tct gct atg aga tct gga ttt ttg ttt        432
Pro Gln Asn His Ile Arg Ile Ser Ala Met Arg Ser Gly Phe Leu Phe
                    115                     120                     125 tat aat tta aca gtt agc gta tct aaa tac cct aaa ttt aaa tcg ctt        480
Tyr Asn Leu Thr Val Ser Val Ser Lys Tyr Pro Lys Phe Lys Ser Leu
                130                     135                     140 caa tgt gtt ggc aat tct aca tct gtc tat tta aat ggt gat ctt gtt        528
Gln Cys Val Gly Asn Ser Thr Ser Val Tyr Leu Asn Gly Asp Leu Val
            145                     150                     155 ttc act tct aat gaa aca act cac gtt acg ggt gca ggc gtt tat ttt        576
Phe Thr Ser Asn Glu Thr Thr His Val Thr Gly Ala Gly Val Tyr Phe
        160                     165                     170 aaa agt ggt ggg cct gta act tat aaa gtt atg aaa gaa gtt aaa gcc        624
Lys Ser Gly Gly Pro Val Thr Tyr Lys Val Met Lys Glu Val Lys Ala
175                     180                     185                     190 cta gcc tac ttt att aat ggt acc gca caa gag gtt att tta tgt gat        672
Leu Ala Tyr Phe Ile Asn Gly Thr Ala Gln Glu Val Ile Leu Cys Asp
                    195                     200                     205 aac tca cct aga ggt ttg ctt gca tgt cag tat aac act ggt aat ttt        720
Asn Ser Pro Arg Gly Leu Leu Ala Cys Gln Tyr Asn Thr Gly Asn Phe
                210                     215                     220 tca gat gga ttc tac cct ttt act aat tct tct tta gtt aag gat agg        768
Ser Asp Gly Phe Tyr Pro Phe Thr Asn Ser Ser Leu Val Lys Asp Arg
            225                     230                     235 ttt att gta tat cga gaa agc agc act aac act act tta gag tta act        816
Phe Ile Val Tyr Arg Glu Ser Ser Thr Asn Thr Thr Leu Glu Leu Thr
        240                     245                     250 aat ttc act ttt act aat gta agt aat gct tct cct aat tca ggt ggc        864
Asn Phe Thr Phe Thr Asn Val Ser Asn Ala Ser Pro Asn Ser Gly Gly
255                     260                     265                     270 gtt gat act ttc caa tta tat caa aca cat act gct cag gat ggt tat        912
Val Asp Thr Phe Gln Leu Tyr Gln Thr His Thr Ala Gln Asp Gly Tyr
                    275                     280                     285 tat aat ttt aat tta tca ttt ctg agt agt ttt gtg tat aaa cca tct        960
Tyr Asn Phe Asn Leu Ser Phe Leu Ser Ser Phe Val Tyr Lys Pro Ser
                290                     295                     300 gat ttt atg tat ggg tca tac cac cca aat tgt aat ttt aga cca gag       1008
Asp Phe Met Tyr Gly Ser Tyr His Pro Asn Cys Asn Phe Arg Pro Glu
            305                     310                     315 aat att aat aat ggc tta tgg ttt aat tca tta tct gtg tca ctt act       1056
Asn Ile Asn Asn Gly Leu Trp Phe Asn Ser Leu Ser Val Ser Leu Thr
        320                     325                     330 tac gga ccc att caa ggt ggt tgt aag caa tct gtt ttt agt aat aaa       1104
Tyr Gly Pro Ile Gln Gly Gly Cys Lys Gln Ser Val Phe Ser Asn Lys
335                     340                     345                     350 gca act tgt tgc tat gct tat tct tac cga ggt cct act aga tgt aag       1152
```

```
                                              -continued

Ala Thr Cys Cys Tyr Ala Tyr Ser Tyr Arg Gly Pro Thr Arg Cys Lys
            355                 360                 365 ggt gtt tat aga ggg gag cta acg caa tac ttt gaa tgt gga ctt cta      1200
Gly Val Tyr Arg Gly Glu Leu Thr Gln Tyr Phe Glu Cys Gly Leu Leu
            370                 375                 380 gtt tat gta act aag agt gat ggc tct cgt ata caa act aga agt gaa      1248
Val Tyr Val Thr Lys Ser Asp Gly Ser Arg Ile Gln Thr Arg Ser Glu
            385                 390                 395 cca ctg gtg tta act caa tat aat tat aac aac att act tta aat aag      1296
Pro Leu Val Leu Thr Gln Tyr Asn Tyr Asn Asn Ile Thr Leu Asn Lys
            400                 405                 410 tgt gtt gag tat aat ata tat ggt aga gtt ggt caa ggt ttt att act      1344
Cys Val Glu Tyr Asn Ile Tyr Gly Arg Val Gly Gln Gly Phe Ile Thr
415                 420                 425                 430 aat gta act gaa gca act gct aat tat agt tat cta gca gat ggt ggt      1392
Asn Val Thr Glu Ala Thr Ala Asn Tyr Ser Tyr Leu Ala Asp Gly Gly
                    435                 440                 445 tta gct att tta gat act tca gga gcc ata gac ata ttt gtt gtt cga      1440
Leu Ala Ile Leu Asp Thr Ser Gly Ala Ile Asp Ile Phe Val Val Arg
                    450                 455                 460 ggt gca tat ggt ctt aat tat tat aag gtt aat ccc tgt gaa gat gtt      1488
Gly Ala Tyr Gly Leu Asn Tyr Tyr Lys Val Asn Pro Cys Glu Asp Val
            465                 470                 475 aac caa cag ttt gta gtg tct ggt gga aat tta gtt ggc att ctt aca      1536
Asn Gln Gln Phe Val Val Ser Gly Gly Asn Leu Val Gly Ile Leu Thr
        480                 485                 490 tct cat aat gaa aca gat tct gaa ttt att gag aac cag ttt tac atc      1584
Ser His Asn Glu Thr Asp Ser Glu Phe Ile Glu Asn Gln Phe Tyr Ile
495                 500                 505                 510 aaa ctc act aac gga aca cgt cgc tct aga cgt tct gtt act ggg aat      1632
Lys Leu Thr Asn Gly Thr Arg Arg Ser Arg Arg Ser Val Thr Gly Asn
                    515                 520                 525 gtt aca aat tgc cct tat gtt agt tat ggc aag ttt tgt ata aaa cca      1680
Val Thr Asn Cys Pro Tyr Val Ser Tyr Gly Lys Phe Cys Ile Lys Pro
                    530                 535                 540 gat ggt tct tta ttt ata ata gta cca caa gag tta gaa cag ttt gtg      1728
Asp Gly Ser Leu Phe Ile Ile Val Pro Gln Glu Leu Glu Gln Phe Val
            545                 550                 555 gcg cct tta ctc aat gtt act gag cat gtg ctc ata cct gat agt ttt      1776
Ala Pro Leu Leu Asn Val Thr Glu His Val Leu Ile Pro Asp Ser Phe
        560                 565                 570 aat tta act gtc aca gat gag tac ata caa act cgt atg gat aag gtt      1824
Asn Leu Thr Val Thr Asp Glu Tyr Ile Gln Thr Arg Met Asp Lys Val
575                 580                 585                 590 caa att aat tgc ctt cag tat gtt tgt ggt aat tct att gaa tgc aga      1872
Gln Ile Asn Cys Leu Gln Tyr Val Cys Gly Asn Ser Ile Glu Cys Arg
                    595                 600                 605 aag ttg ttt cag cag tat gga cct gtt tgt gat aat ata ttg tct gtt      1920
Lys Leu Phe Gln Gln Tyr Gly Pro Val Cys Asp Asn Ile Leu Ser Val
                    610                 615                 620 gta aat ggt gta ggt caa aga gag gat atg gaa ctt tta agt ttc tat      1968
Val Asn Gly Val Gly Gln Arg Glu Asp Met Glu Leu Leu Ser Phe Tyr
            625                 630                 635 tcg tct act aaa cct agt ggt tac aat aca cca att ttt aat aat gtt      2016
Ser Ser Thr Lys Pro Ser Gly Tyr Asn Thr Pro Ile Phe Asn Asn Val
        640                 645                 650 agc act ggt gac ttt aat att tct ctc cta cta aca cca cct aat agt      2064
Ser Thr Gly Asp Phe Asn Ile Ser Leu Leu Leu Thr Pro Pro Asn Ser
655                 660                 665                 670
```

-continued

```
cct act ggg cgc tct ttt att gaa gat ctt ctt ttt aca agt gta gaa       2112
Pro Thr Gly Arg Ser Phe Ile Glu Asp Leu Leu Phe Thr Ser Val Glu
                675             680             685 tct gtt gga tta cca act gat gaa gag tat aaa aag tgt aca gca gga       2160
Ser Val Gly Leu Pro Thr Asp Glu Glu Tyr Lys Lys Cys Thr Ala Gly
        690             695             700 cct tta ggt ttt gtt aag gac ctt gtt tgt gct aga gag tat aat ggc       2208
Pro Leu Gly Phe Val Lys Asp Leu Val Cys Ala Arg Glu Tyr Asn Gly
    705             710             715 ttg ctt gtg ttg cct cct att att act gca gac atg caa act atg tat       2256
Leu Leu Val Leu Pro Pro Ile Ile Thr Ala Asp Met Gln Thr Met Tyr
720             725             730 act agc tct tta gta gcc tct atg gct tta ggt ggc att act gca gct       2304
Thr Ser Ser Leu Val Ala Ser Met Ala Leu Gly Gly Ile Thr Ala Ala
735             740             745             750 ggt gct ata cct ttt gct aca caa ctg cag gcc aga att aac cat ttg       2352
Gly Ala Ile Pro Phe Ala Thr Gln Leu Gln Ala Arg Ile Asn His Leu
                755             760             765 ggt att act aat tct ctt ttg ttg aaa aat caa gaa aaa att gct gct       2400
Gly Ile Thr Asn Ser Leu Leu Leu Lys Asn Gln Glu Lys Ile Ala Ala
        770             775             780 tcc ttt aat aag gcc atc ggt cat atg cag gga ggg ttt aaa agt act       2448
Ser Phe Asn Lys Ala Ile Gly His Met Gln Gly Gly Phe Lys Ser Thr
    785             790             795 tct cta gca tta caa cag att caa gat gtt gtt aat aaa cag agt tct       2496
Ser Leu Ala Leu Gln Gln Ile Gln Asp Val Val Asn Lys Gln Ser Ser
800             805             810 att ctt aca gag act atg caa tca ctt aat aaa aat ttt ggt gct att       2544
Ile Leu Thr Glu Thr Met Gln Ser Leu Asn Lys Asn Phe Gly Ala Ile
815             820             825             830 tcc tcc gta ctt caa gac att tac cag caa ctt gat gct att cag gca       2592
Ser Ser Val Leu Gln Asp Ile Tyr Gln Gln Leu Asp Ala Ile Gln Ala
                835             840             845 gat gct cag gtt gat cgt ctt att aca ggt aga ctt tct tca cta tct       2640
Asp Ala Gln Val Asp Arg Leu Ile Thr Gly Arg Leu Ser Ser Leu Ser
        850             855             860 gtt tta gct tct gct aaa cag gca gag tat cat aga gtg tca caa cag       2688
Val Leu Ala Ser Ala Lys Gln Ala Glu Tyr His Arg Val Ser Gln Gln
    865             870             875 cgt gag ttg gcc act cag aaa att aat gag tgt gtt aag tct cag tct       2736
Arg Glu Leu Ala Thr Gln Lys Ile Asn Glu Cys Val Lys Ser Gln Ser
880             885             890 aat agg tat tca ttt tgt ggt aat gga aga cat gtt tta acc ata cca       2784
Asn Arg Tyr Ser Phe Cys Gly Asn Gly Arg His Val Leu Thr Ile Pro
895             900             905             910 caa aat gca cct aat ggt ata gtg ttt ata cac ttt act tat act cca       2832
Gln Asn Ala Pro Asn Gly Ile Val Phe Ile His Phe Thr Tyr Thr Pro
                915             920             925 gag agt ttt gtt aat gtt act gca ata gtg ggt ttt tgt gta aat cca       2880
Glu Ser Phe Val Asn Val Thr Ala Ile Val Gly Phe Cys Val Asn Pro
        930             935             940 gct aat gcc agt cag tat gca ata gtg ccc gtt aat aac aga ggt att       2928
Ala Asn Ala Ser Gln Tyr Ala Ile Val Pro Val Asn Asn Arg Gly Ile
    945             950             955 ttt att caa gtt aat ggt agt tac tac atc act gca cgt gat atg tat       2976
Phe Ile Gln Val Asn Gly Ser Tyr Tyr Ile Thr Ala Arg Asp Met Tyr
960             965             970 atg cca aga gac att aca gca gga gac ata gtt acg ctt act tct tgt       3024
Met Pro Arg Asp Ile Thr Ala Gly Asp Ile Val Thr Leu Thr Ser Cys
975             980             985             990
```

```
caa gca aat tat gta agt gta aat aag act gtc att act aca ttt gta    3072
Gln Ala Asn Tyr Val Ser Val Asn Lys Thr Val Ile Thr Thr Phe Val
                995                1000               1005 gat aat gat gac ttt gat ttt gat gac gaa ttg tca aaa tgg tgg        3117
Asp Asn Asp Asp Phe Asp Phe Asp Asp Glu Leu Ser Lys Trp Trp
            1010            1015               1020 aat gat act aag cat gag cta cca gat ttc gac gaa ttc aat tat        3162
Asn Asp Thr Lys His Glu Leu Pro Asp Phe Asp Glu Phe Asn Tyr
        1025                1030               1035 aca gta cca gta tta aat att agt aat gaa att gac aga att caa        3207
Thr Val Pro Val Leu Asn Ile Ser Asn Glu Ile Asp Arg Ile Gln
        1040                1045               1050 gaa gtt att cag gga tta aat gac tcc cta ata gat ctt gaa aca        3252
Glu Val Ile Gln Gly Leu Asn Asp Ser Leu Ile Asp Leu Glu Thr
        1055                1060               1065 ctc tca att ctt aaa act tat att aag tgg cct tgg tat gtg tgg        3297
Leu Ser Ile Leu Lys Thr Tyr Ile Lys Trp Pro Trp Tyr Val Trp
        1070                1075               1080 ctt gcc ata gct ttt gcc att att atc ttc atc cta atc tta gga        3342
Leu Ala Ile Ala Phe Ala Ile Ile Ile Phe Ile Leu Ile Leu Gly
        1085                1090               1095 tgg gtt ttc ttc atg act ggt tgt tgt ggt tgt tgt tgt ggg tgc        3387
Trp Val Phe Phe Met Thr Gly Cys Cys Gly Cys Cys Cys Gly Cys
        1100                1105               1110 ttc ggc att att cct tta atg agt aag tgt ggt aaa aaa tct tct        3432
Phe Gly Ile Ile Pro Leu Met Ser Lys Cys Gly Lys Lys Ser Ser
        1115                1120               1125 tac tac acg act ttt gat aat gat gtg gta act gaa caa tac aga        3477
Tyr Tyr Thr Thr Phe Asp Asn Asp Val Val Thr Glu Gln Tyr Arg
        1130                1135               1140 cct aaa aag tct gtt taatga                                         3498
Pro Lys Lys Ser Val
        1145

<210> SEQ ID NO 2
<211> LENGTH: 1164
<212> TYPE: PRT
<213> ORGANISM: Infectious bronchitis virus

<400> SEQUENCE: 2

Met Leu Gly Lys Pro Leu Leu Val Thr Leu Trp Tyr Ala Leu Cys
            -15            -10                -5

Ser Ala Leu Leu Tyr Asp Lys Asn Thr Tyr Val Tyr Tyr Gln Ser
     -1  1            5                  10

Ala Phe Arg Pro Gly Gln Gly Trp His Leu His Gly Gly Ala Tyr Ala
 15               20              25                  30

Val Asp Lys Val Phe Asn Gly Thr Asn Asn Ala Val Ser Val Ser Asp
             35              40                  45

Cys Thr Ala Gly Thr Phe Tyr Glu Ser Tyr Asn Ile Ser Ala Ala Ser
             50              55                  60

Val Ala Met Thr Val Pro Pro Ala Gly Met Ser Trp Ser Val Ser Gln
         65              70                  75

Phe Cys Thr Ala His Cys Asn Phe Ser Asp Phe Thr Val Phe Val Thr
     80              85                  90

His Cys Phe Lys Ser Gln Gln Gly Ser Cys Pro Leu Thr Gly Met Ile
 95              100                 105                 110

Pro Gln Asn His Ile Arg Ile Ser Ala Met Arg Ser Gly Phe Leu Phe
             115                 120                 125
```

-continued

```
Tyr Asn Leu Thr Val Ser Val Ser Lys Tyr Pro Lys Phe Lys Ser Leu
            130                 135                 140

Gln Cys Val Gly Asn Ser Thr Ser Val Tyr Leu Asn Gly Asp Leu Val
        145                 150                 155

Phe Thr Ser Asn Glu Thr Thr His Val Thr Gly Ala Gly Val Tyr Phe
    160                 165                 170

Lys Ser Gly Gly Pro Val Thr Tyr Lys Val Met Lys Glu Val Lys Ala
175                 180                 185                 190

Leu Ala Tyr Phe Ile Asn Gly Thr Ala Gln Glu Val Ile Leu Cys Asp
                195                 200                 205

Asn Ser Pro Arg Gly Leu Leu Ala Cys Gln Tyr Asn Thr Gly Asn Phe
            210                 215                 220

Ser Asp Gly Phe Tyr Pro Phe Thr Asn Ser Ser Leu Val Lys Asp Arg
        225                 230                 235

Phe Ile Val Tyr Arg Glu Ser Ser Thr Asn Thr Thr Leu Glu Leu Thr
    240                 245                 250

Asn Phe Thr Phe Thr Asn Val Ser Asn Ala Ser Pro Asn Ser Gly Gly
255                 260                 265                 270

Val Asp Thr Phe Gln Leu Tyr Gln Thr His Thr Ala Gln Asp Gly Tyr
                275                 280                 285

Tyr Asn Phe Asn Leu Ser Phe Leu Ser Ser Phe Val Tyr Lys Pro Ser
            290                 295                 300

Asp Phe Met Tyr Gly Ser Tyr His Pro Asn Cys Asn Phe Arg Pro Glu
        305                 310                 315

Asn Ile Asn Asn Gly Leu Trp Phe Asn Ser Leu Ser Val Ser Leu Thr
    320                 325                 330

Tyr Gly Pro Ile Gln Gly Gly Cys Lys Gln Ser Val Phe Ser Asn Lys
335                 340                 345                 350

Ala Thr Cys Cys Tyr Ala Tyr Ser Tyr Arg Gly Pro Thr Arg Cys Lys
                355                 360                 365

Gly Val Tyr Arg Gly Glu Leu Thr Gln Tyr Phe Glu Cys Gly Leu Leu
            370                 375                 380

Val Tyr Val Thr Lys Ser Asp Gly Ser Arg Ile Gln Thr Arg Ser Glu
        385                 390                 395

Pro Leu Val Leu Thr Gln Tyr Asn Tyr Asn Asn Ile Thr Leu Asn Lys
    400                 405                 410

Cys Val Glu Tyr Asn Ile Tyr Gly Arg Val Gly Gln Gly Phe Ile Thr
415                 420                 425                 430

Asn Val Thr Glu Ala Thr Ala Asn Tyr Ser Tyr Leu Ala Asp Gly Gly
                435                 440                 445

Leu Ala Ile Leu Asp Thr Ser Gly Ala Ile Asp Ile Phe Val Val Arg
            450                 455                 460

Gly Ala Tyr Gly Leu Asn Tyr Tyr Lys Val Asn Pro Cys Glu Asp Val
        465                 470                 475

Asn Gln Gln Phe Val Val Ser Gly Gly Asn Leu Val Gly Ile Leu Thr
    480                 485                 490

Ser His Asn Glu Thr Asp Ser Glu Phe Ile Glu Asn Gln Phe Tyr Ile
495                 500                 505                 510

Lys Leu Thr Asn Gly Thr Arg Arg Ser Arg Ser Val Thr Gly Asn
                515                 520                 525

Val Thr Asn Cys Pro Tyr Val Ser Tyr Gly Lys Phe Cys Ile Lys Pro
            530                 535                 540
```

-continued

```
Asp Gly Ser Leu Phe Ile Ile Val Pro Gln Glu Leu Glu Gln Phe Val
        545                 550                 555

Ala Pro Leu Leu Asn Val Thr Glu His Val Leu Ile Pro Asp Ser Phe
        560                 565                 570

Asn Leu Thr Val Thr Asp Glu Tyr Ile Gln Thr Arg Met Asp Lys Val
575                 580                 585                 590

Gln Ile Asn Cys Leu Gln Tyr Val Cys Gly Asn Ser Ile Glu Cys Arg
                595                 600                 605

Lys Leu Phe Gln Gln Tyr Gly Pro Val Cys Asp Asn Ile Leu Ser Val
                610                 615                 620

Val Asn Gly Val Gly Gln Arg Glu Asp Met Glu Leu Leu Ser Phe Tyr
        625                 630                 635

Ser Ser Thr Lys Pro Ser Gly Tyr Asn Thr Pro Ile Phe Asn Asn Val
        640                 645                 650

Ser Thr Gly Asp Phe Asn Ile Ser Leu Leu Thr Pro Pro Asn Ser
655                 660                 665                 670

Pro Thr Gly Arg Ser Phe Ile Glu Asp Leu Leu Phe Thr Ser Val Glu
                675                 680                 685

Ser Val Gly Leu Pro Thr Asp Glu Glu Tyr Lys Lys Cys Thr Ala Gly
        690                 695                 700

Pro Leu Gly Phe Val Lys Asp Leu Val Cys Ala Arg Glu Tyr Asn Gly
        705                 710                 715

Leu Leu Val Leu Pro Pro Ile Ile Thr Ala Asp Met Gln Thr Met Tyr
        720                 725                 730

Thr Ser Ser Leu Val Ala Ser Met Ala Leu Gly Gly Ile Thr Ala Ala
735                 740                 745                 750

Gly Ala Ile Pro Phe Ala Thr Gln Leu Gln Ala Arg Ile Asn His Leu
                755                 760                 765

Gly Ile Thr Asn Ser Leu Leu Leu Lys Asn Gln Glu Lys Ile Ala Ala
                770                 775                 780

Ser Phe Asn Lys Ala Ile Gly His Met Gln Gly Gly Phe Lys Ser Thr
785                 790                 795

Ser Leu Ala Leu Gln Gln Ile Gln Asp Val Val Asn Lys Gln Ser Ser
        800                 805                 810

Ile Leu Thr Glu Thr Met Gln Ser Leu Asn Lys Asn Phe Gly Ala Ile
815                 820                 825                 830

Ser Ser Val Leu Gln Asp Ile Tyr Gln Gln Leu Asp Ala Ile Gln Ala
                835                 840                 845

Asp Ala Gln Val Asp Arg Leu Ile Thr Gly Arg Leu Ser Ser Leu Ser
        850                 855                 860

Val Leu Ala Ser Ala Lys Gln Ala Glu Tyr His Arg Val Ser Gln Gln
        865                 870                 875

Arg Glu Leu Ala Thr Gln Lys Ile Asn Glu Cys Val Lys Ser Gln Ser
        880                 885                 890

Asn Arg Tyr Ser Phe Cys Gly Asn Gly Arg His Val Leu Thr Ile Pro
895                 900                 905                 910

Gln Asn Ala Pro Asn Gly Ile Val Phe Ile His Phe Thr Tyr Thr Pro
                915                 920                 925

Glu Ser Phe Val Asn Val Thr Ala Ile Val Gly Phe Cys Val Asn Pro
        930                 935                 940

Ala Asn Ala Ser Gln Tyr Ala Ile Val Pro Val Asn Asn Arg Gly Ile
        945                 950                 955

Phe Ile Gln Val Asn Gly Ser Tyr Tyr Ile Thr Ala Arg Asp Met Tyr
```

-continued

```
            960                 965                 970
Met Pro Arg Asp Ile Thr Ala Gly Asp Ile Val Thr Leu Thr Ser Cys
975                 980                 985                 990

Gln Ala Asn Tyr Val Ser Val Asn Lys Thr  Val Ile Thr Thr Phe  Val
                995                 1000                1005

Asp Asn Asp Asp  Phe Asp Phe Asp  Asp  Glu Leu Ser Lys Trp    Trp
            1010             1015                 1020

Asn Asp Thr Lys  His Glu Leu Pro Asp  Phe Asp Glu Phe Asn  Tyr
            1025             1030                 1035

Thr Val Pro Val  Leu Asn Ile Ser Asn  Glu Ile Asp Arg Ile  Gln
            1040             1045                 1050

Glu Val Ile Gln  Gly Leu Asn Asp Ser  Leu Ile Asp Leu Glu  Thr
            1055             1060                 1065

Leu Ser Ile Leu  Lys Thr Tyr Ile Lys  Trp Pro Trp Tyr Val  Trp
            1070             1075                 1080

Leu Ala Ile Ala  Phe Ala Ile Ile Ile  Phe Ile Leu Ile Leu  Gly
            1085             1090                 1095

Trp Val Phe Phe  Met Thr Gly Cys Cys  Gly Cys Cys Cys Gly  Cys
            1100             1105                 1110

Phe Gly Ile Ile  Pro Leu Met Ser Lys  Cys Gly Lys Lys Ser  Ser
            1115             1120                 1125

Tyr Tyr Thr Thr  Phe Asp Asn Asp Val  Val Thr Glu Gln Tyr  Arg
            1130             1135                 1140

Pro Lys Lys Ser  Val
            1145
```